(12) United States Patent
Theodorou

(10) Patent No.: US 10,973,712 B2
(45) Date of Patent: *Apr. 13, 2021

(54) IFAK PACKAGE ASSEMBLIES

(71) Applicant: Peter Theodorou, Opa-locka, FL (US)

(72) Inventor: Peter Theodorou, Opa-locka, FL (US)

(73) Assignee: Red Stripe, Opa Locka, FL (US)

(*) Notice: Subject to any disclaimer, the term of this patent is extended or adjusted under 35 U.S.C. 154(b) by 72 days.

This patent is subject to a terminal disclaimer.

(21) Appl. No.: 16/353,080

(22) Filed: Mar. 14, 2019

(65) Prior Publication Data

US 2020/0289348 A1    Sep. 17, 2020

(51) Int. Cl.
*A61F 17/00*    (2006.01)
*A61B 17/132*    (2006.01)

(52) U.S. Cl.
CPC ............ *A61F 17/00* (2013.01); *A61B 17/132* (2013.01)

(58) Field of Classification Search
CPC ........ A61F 17/00; A61F 17/132; A61F 50/30; A61F 50/1026; A61F 19/0271; A45C 3/001; A45C 7/0077; A45C 7/0086; A45C 7/009
USPC ...... 206/570–572, 38, 528, 803; 383/14, 76, 383/67, 38–41
See application file for complete search history.

(56) References Cited

U.S. PATENT DOCUMENTS 1,745,590 A    2/1930 Stanger
4,386,642 A *   6/1983 Durbin ..................... A45C 3/00
                                                   190/110
4,979,614 A *  12/1990 Ruhaut ................ B65H 75/362
                                                   174/135

(Continued)

FOREIGN PATENT DOCUMENTS

DE      200920017918     8/2010
DE      202014007690 U1  9/2014
WO  PCT/AU1993/000184   11/1993

*Primary Examiner* — Chun Hoi Cheung
(74) *Attorney, Agent, or Firm* — R. Keith Harrison

(57) ABSTRACT

IFAK assemblies may include an outer shell having a first outer shell end, a second outer shell end, an outer shell interior extending between the first outer shell end and the second outer shell end, a first shell opening at the first outer shell end and a second shell opening at the second outer shell end. An interior sleeve may be removably deployed in the outer shell interior of the outer shell. The interior sleeve may be selectively removable from a selected one of the first shell opening and the second shell opening. A plurality of first aid items may be carried by the interior sleeve. A left tourniquet sleeve may be carried by a first side of the outer shell. The left tourniquet sleeve may have a left sleeve interior configured to contain at least one left tourniquet and a left tourniquet retrieval opening corresponding in position to the first outer shell end of the outer shell. At least one left sleeve compression band may be provided in the left tourniquet sleeve. A right tourniquet sleeve may be carried by a second side of the outer shell opposite the first side. The right tourniquet sleeve may have a right sleeve interior configured to contain at least one right tourniquet and a right tourniquet retrieval opening corresponding in position to the second outer shell end of the outer shell. At least one right sleeve compression band may be provided in the right tourniquet sleeve.

20 Claims, 24 Drawing Sheets

(56) References Cited

U.S. PATENT DOCUMENTS

| | | | | |
|---|---|---|---|---|
| 5,207,303 | A * | 5/1993 | Oswalt | A61B 50/312 190/108 |
| 5,451,108 | A * | 9/1995 | Anderson | B65D 31/12 383/38 |
| 5,692,836 | A * | 12/1997 | Mitchell | B65F 1/0006 383/22 |
| 6,085,695 | A | 7/2000 | Miller et al. | |
| 6,190,045 | B1 * | 2/2001 | Schulman | B65D 33/1616 383/24 |
| 6,516,981 | B2 * | 2/2003 | Perez | A41D 13/0012 2/102 |
| 7,344,308 | B2 * | 3/2008 | Meyer | A63B 57/60 383/41 |
| 8,602,073 | B2 | 12/2013 | Swain | |
| 8,647,123 | B1 * | 2/2014 | Carter | G16H 40/63 434/262 |
| 9,333,128 | B2 | 5/2016 | Catrone | |
| 10,595,878 | B2 * | 3/2020 | Theodorou | A61B 17/1322 |
| 2003/0155268 | A1 * | 8/2003 | Wang | A45C 3/001 206/522 |
| 2005/0161483 | A1 | 7/2005 | Krohn et al. | |
| 2007/0131573 | A1 * | 6/2007 | Boyles | A61B 50/31 206/438 |
| 2008/0121554 | A1 * | 5/2008 | Townsend | A45C 5/02 206/570 |
| 2011/0204114 | A1 | 8/2011 | Miller | |
| 2016/0015157 | A1 | 1/2016 | Nouri | |

* cited by examiner

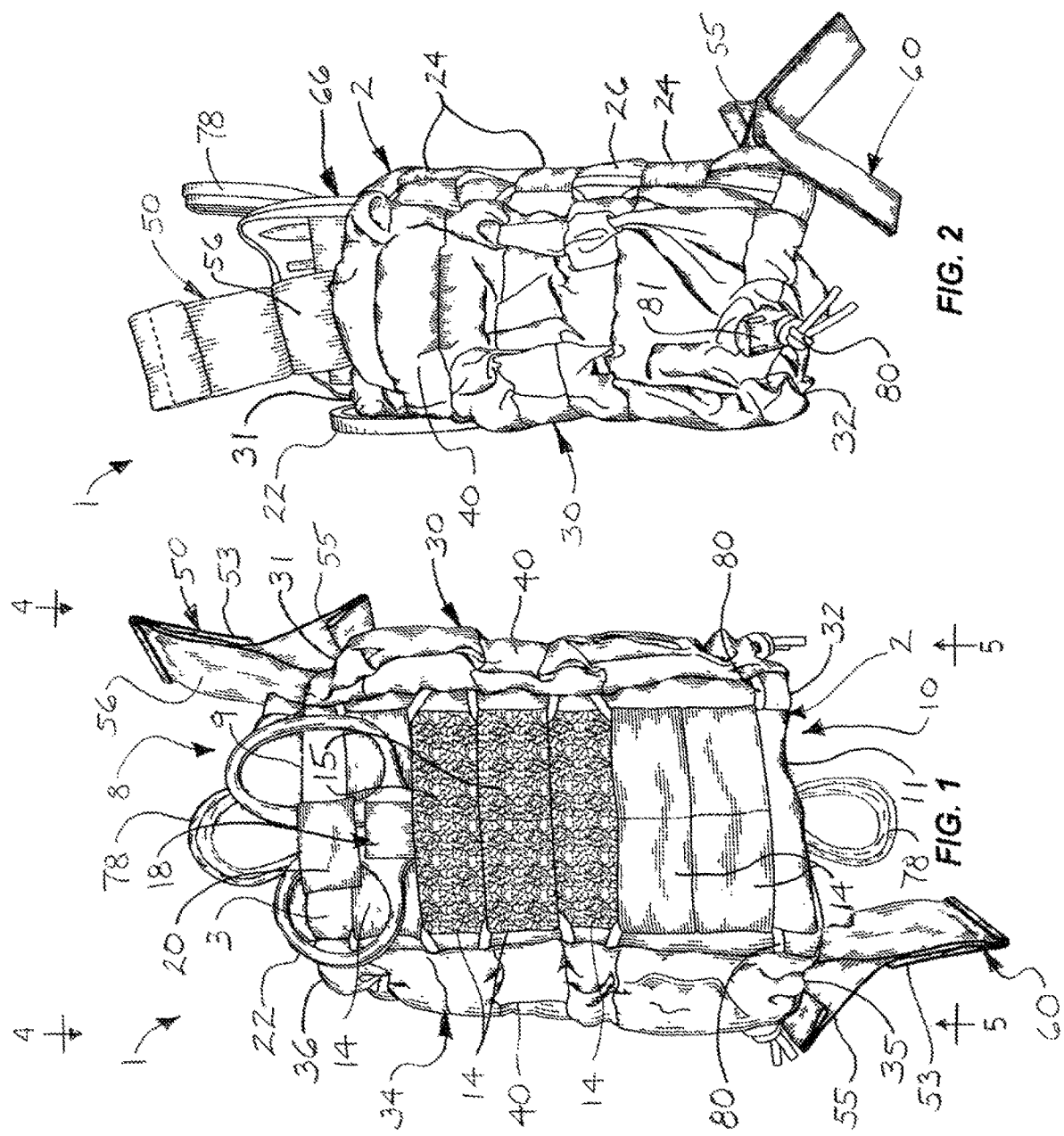

IFAK PACKAGE ASSEMBLIES

FIELD

Illustrative embodiments of the disclosure relate to IFAKs (Individual First Aid Kits). More particularly, illustrative embodiments of the disclosure relate to IFAK package assemblies which may be compatible with MOLLE (Modular Lightweight Load-carrying Equipment) frequently used by law enforcement and military personnel and which facilitate ambidextrous access capability.

SUMMARY

Illustrative embodiments of the disclosure are generally directed to IFAK (individual first aid kit) package assemblies which may be compatible with MOLLE (Modular Lightweight Load-carrying Equipment) frequently used by law enforcement and military personnel and which facilitate ambidextrous access capability. An illustrative embodiment of the IFAK assemblies may include an outer shell having a first outer shell end, a second outer shell end, an outer shell interior extending between the first outer shell end and the second outer shell end, a first shell opening at the first outer shell end and a second shell opening at the second outer shell end. An interior sleeve may be removably deployed in the outer shell interior of the outer shell. The interior sleeve may be selectively removable from a selected one of the first shell opening and the second shell opening. A plurality of first aid items may be carried by the interior sleeve. A left tourniquet sleeve may be carried by a first side of the outer shell. The left tourniquet sleeve may have a left sleeve interior configured to contain at least one left tourniquet and a left tourniquet retrieval opening corresponding in position to the first outer shell end of the outer shell. At least one left sleeve compression band may be provided in the left tourniquet sleeve. A right tourniquet sleeve may be carried by a second side of the outer shell opposite the first side. The right tourniquet sleeve may have a right sleeve interior configured to contain at least one right tourniquet and a right tourniquet retrieval opening corresponding in position to the second outer shell end of the outer shell. At least one right sleeve compression band may be provided in the right tourniquet sleeve.

BRIEF DESCRIPTION OF THE DRAWINGS

Illustrative embodiments of the disclosure will now be described, by way of example, with reference to the accompanying drawings, in which:

FIG. 1 is a front view of an illustrative embodiment of the IFAK package assemblies;

FIG. 2 is a left side view of an illustrative IFAK package assembly;

DETAILED DESCRIPTION

Figure 3:
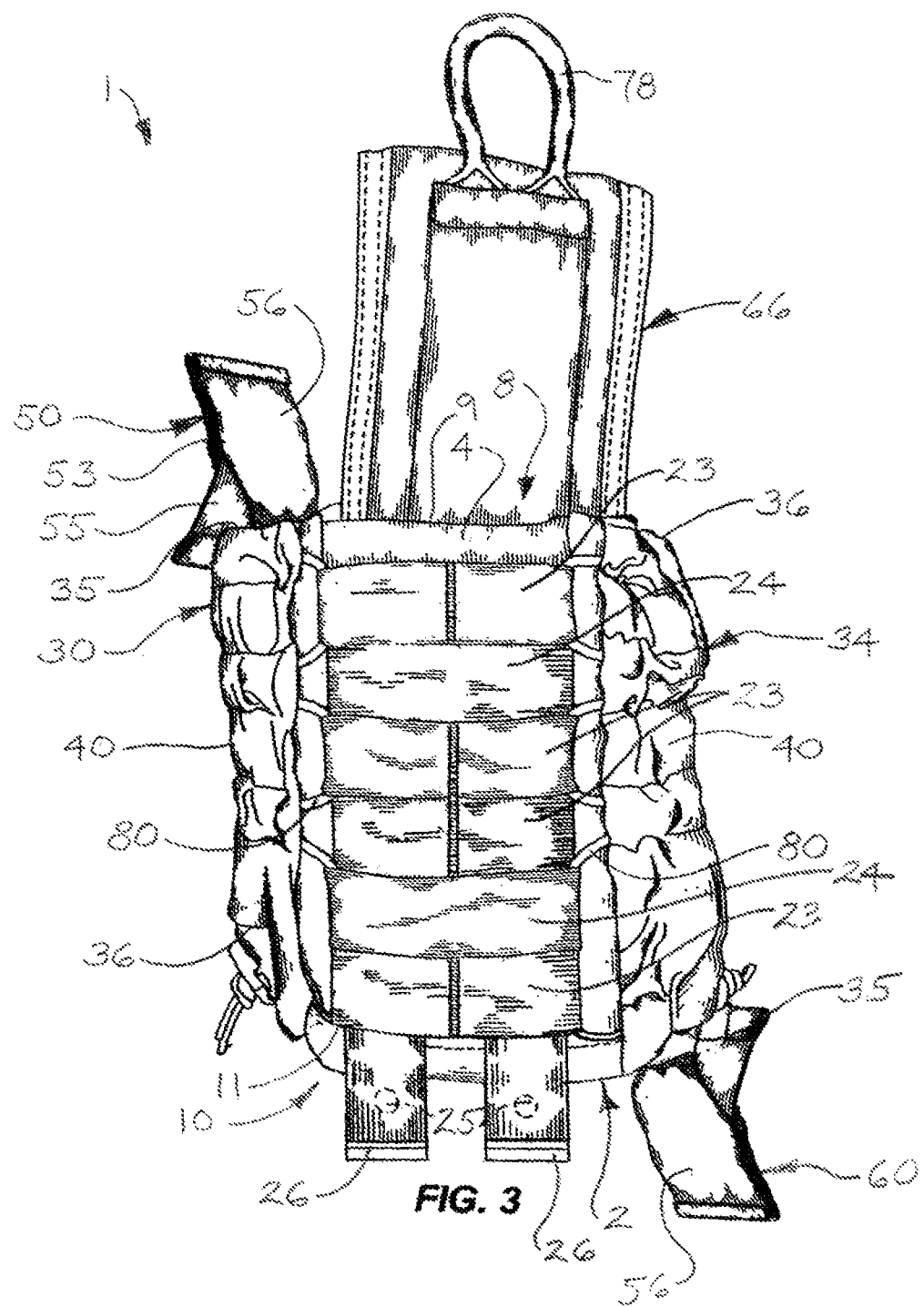
FIG. 3 is a rear view of an illustrative IFAK package assembly, with an interior sleeve shown partially removed from an outer shell of the assembly.

The following detailed description is merely exemplary in nature and is, not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Referring to the drawings, an illustrative embodiment of the IFAK (Individual First Aid Kit) package assembly, hereinafter assembly, is generally indicated by reference numeral 1. As will be hereinafter further described, the assembly 1 may be compatible with MOLLE (Modular Lightweight Load-carrying Equipment) (not illustrated) which is frequently used by law enforcement and military personnel and may provide a user with ambidextrous access to various first aid supplies.

Figure 8:
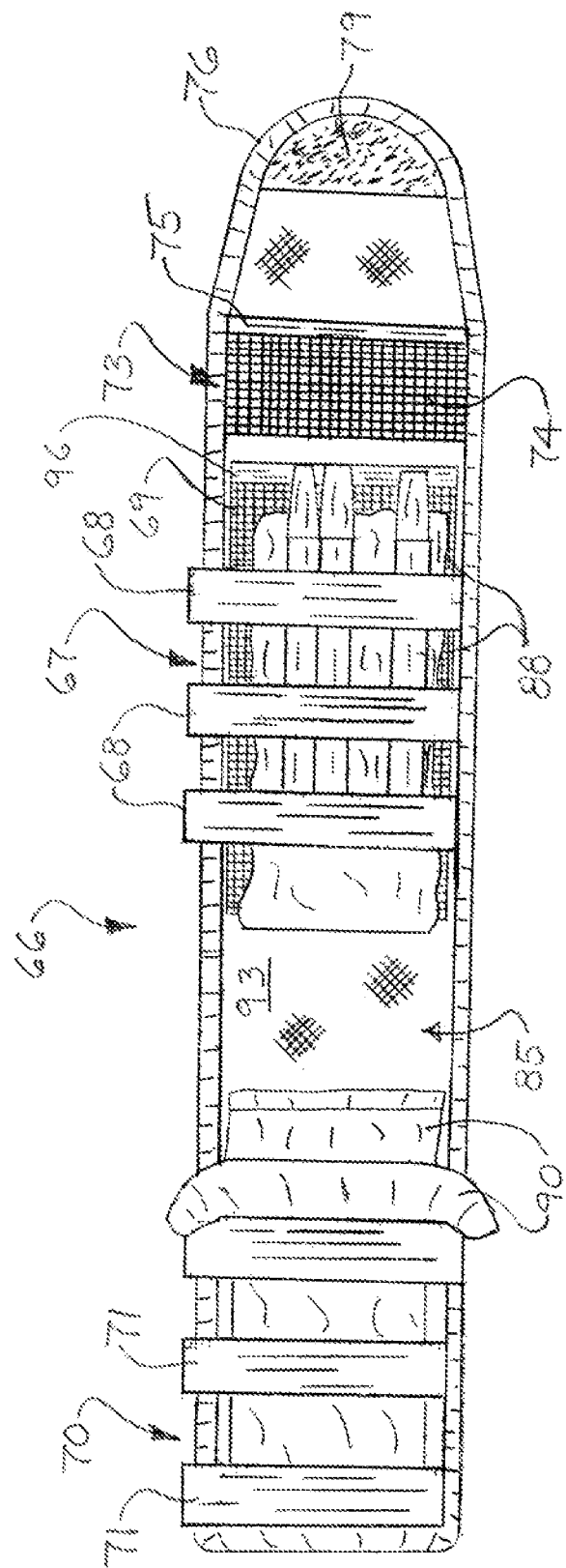
FIG. 8 is an interior view of the illustrative interior sleeve of the IFAK package assembly illustrated in FIG. 7, deployed in the extended configuration, with various first aid items secured in the interior sleeve.
Figure 11:
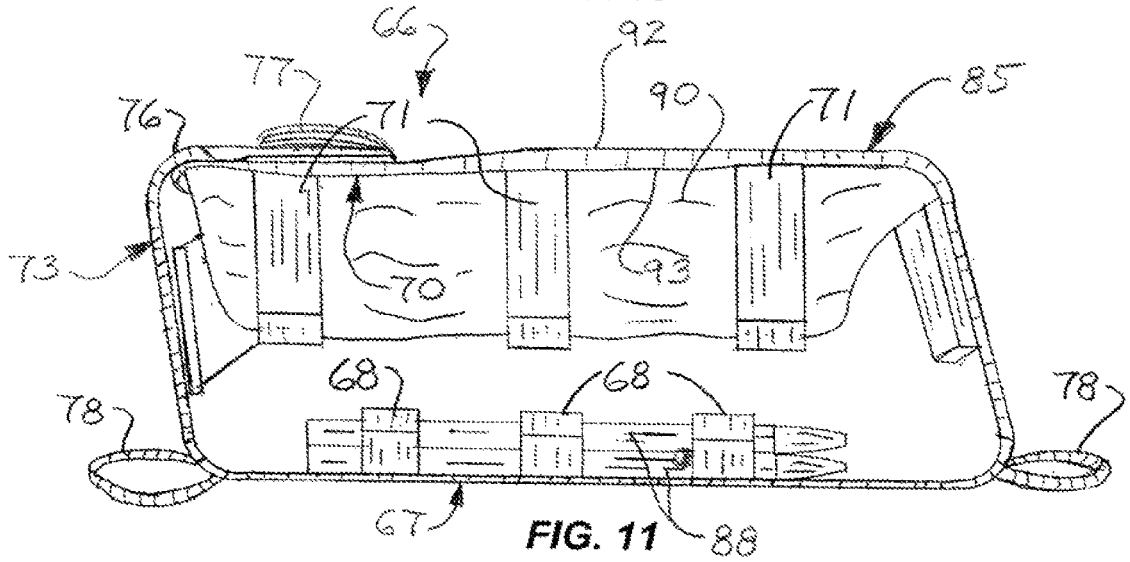
FIG. 11 is a side view of the illustrative interior sleeve deployed in the folded configuration.

As illustrated in FIGS. 1-6, the assembly 1 may include an outer shell 2. An interior sleeve 66 may be normally contained inside and selectively removable from the outer shell 2. As illustrated in FIGS. 8 and 11 and will be hereinafter described, the interior sleeve 66 may contain various first aid items 88, 90 which may be selectively retrieved from the interior sleeve 66 for use. The interior sleeve 66 may be selectively removable from either end of the outer shell 2. Thus, the interior sleeve 66 may facilitate ambidextrous access for easy and expeditious removal from the outer shell 2 by either a left-handed or a right-handed user irrespective of the side of the body on which the assembly 1 is mounted.

As illustrated in FIGS. 1-3, the outer shell 2 of the assembly 1 may include a left tourniquet sleeve 30 and a right tourniquet sleeve 34. The left tourniquet sleeve 30 and the right tourniquet sleeve 34 may be provided on opposite sides of the outer shell 2. The left tourniquet sleeve 30 and the right tourniquet sleeve 34 may each contain a tourniquet 62 (illustrated in phantom in FIGS. 12-14). In some embodiments, the tourniquet 62 may be a C.A.T type tourniquet known by those skilled in the art. The left tourniquet sleeve 30 and the right tourniquet sleeve 34 may be oriented in opposite directions on the outer shell 2 to provide ambidextrous access of a user to each tourniquet 62 from either side of the outer shell 2. Accordingly, the left tourniquet sleeve 30 and the right tourniquet sleeve 34 may facilitate easy and expeditious removal of a tourniquet 62 by either a left-handed or a right-handed user irrespective of the side of the body on which the assembly 1 is mounted.

Figure 4:
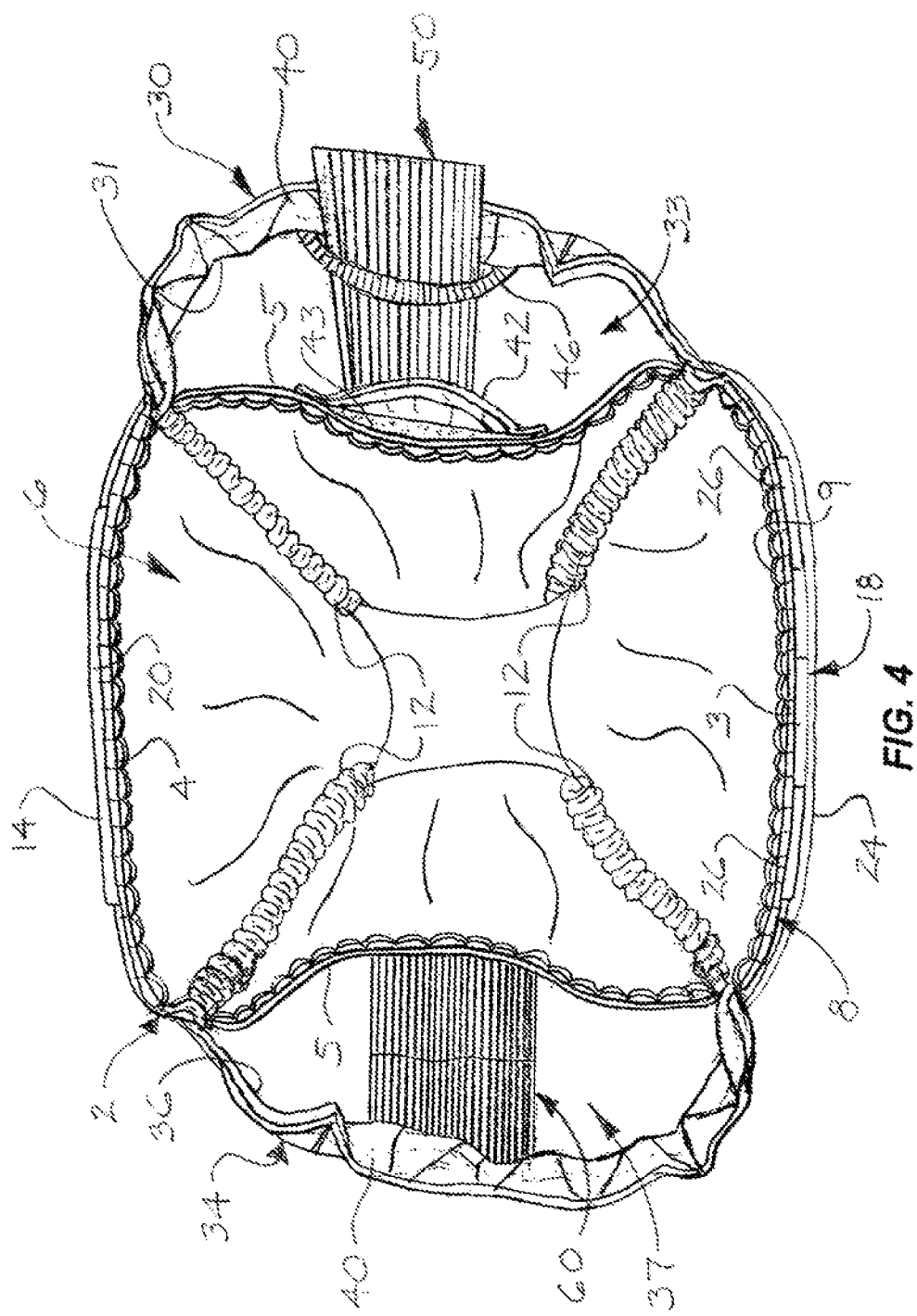
FIG. 4 is a top view, taken along viewing lines 4-4 in FIG. 1, of the outer shell of an illustrative IFAK package assembly, with the interior sleeve (not shown) removed from the outer shell and tourniquets (not shown) removed from respective tourniquet sleeves on the outer shell and the outer shell and tourniquet sleeves shown in a partially-collapsed configuration.
Figure 5:
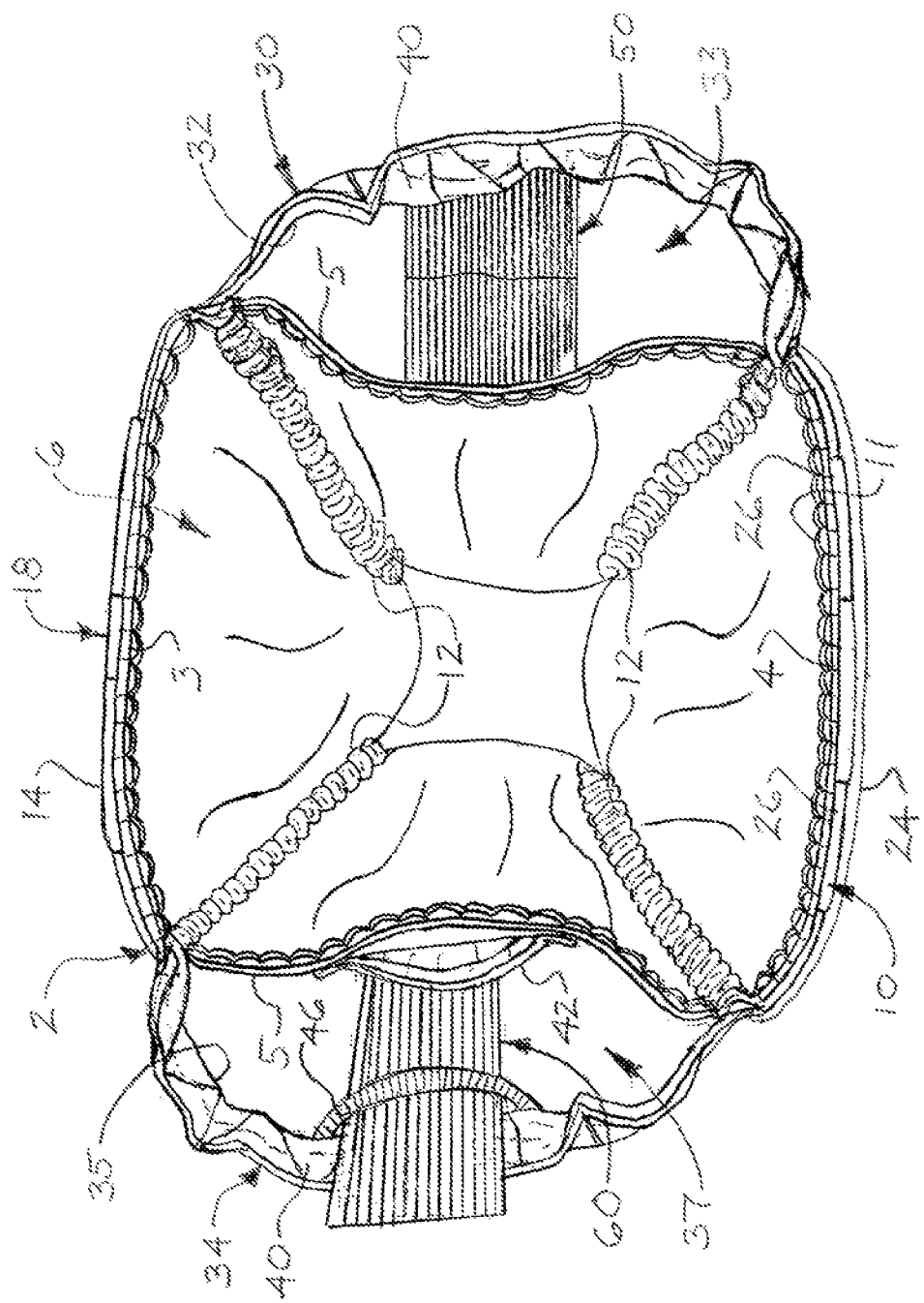
FIG. 5 is a bottom view, taken along viewing lines 5-5 in FIG. 1 of the outer shell of an illustrative IFAK package assembly, with the interior sleeve (not shown) removed from the outer shell and the tourniquets (not shown) removed from the respective tourniquet sleeves in the outer shell and the outer shell and tourniquet sleeves in a partially-collapsed configuration.

As illustrated in FIGS. 4 and 5, the outer shell 2 of the assembly 1 may include a front outer shell wall 3 and a rear outer shell wall 4. A pair of spaced-apart side outer shell walls 5 may extend between the front outer shell wall 3 and the rear outer shell wall 4. In some embodiments, the front outer shell wall 3, the rear outer shell wall 4 and the side outer shell walls 5 may each have multiple layers. An outer shell interior 6 may be formed by and between the front outer shell wall 3, the rear outer shell wall 4 and the side outer shell walls 5. In the assembly 1, the outer shell interior 6 of the outer shell 2 may normally contain the interior sleeve 66 for stowage and transport. Each of the front outer shell wall 3, the rear outer shell wall 4 and the side outer shell walls 5 may have an elastic or stretchable construction. Elastic seams 12 may join the side outer shell walls 5 to the front outer shell wall 3 and the rear outer shell will 4, Accordingly, the outer shell 2 may be elastic and stretchable to impart a variable volume to the outer shell interior 6 and facilitate securement of the interior sleeve 6 in the outer shell interior 6. The outer shell 2 may be fabricated of any suitable type of durable fabric material known by those skilled in the art.

As further illustrated in FIGS. 1-6, the outer shell 2 may be generally elongated in shape and, may have a first outer shell end 8 and a second outer shell end 10. The first outer shell end 8 may have a first shell opening 9 which communicates with the outer shell interior 6 (FIGS. 4 and 5). The second outer shell end 10 may have a second shell opening 11 which communicates with the outer shell interior 6.

The left tourniquet sleeve 30 may extend along a left side of the outer shell 2, Similarly, the right tourniquet sleeve 34 may extend along, a right side of the outer shell 2. As illustrated in FIGS. 4 and 5, each of the left tourniquet sleeve 30 and the right tourniquet sleeve 34 may have an outer sleeve wall 40. The outer sleeve wall 40 may be sewn, attached to or fabricated in one niece with each corresponding side outer shell wall 5 of the outer shell 2 according to the knowledge of those skilled in the art. The outer sleeve wall 40 may have multiple layers and may have an elastic and stretchable construction.

As further illustrated in FIGS. 4 and 5, left tourniquet sleeve 30 may have a left sleeve interior 33 and the right tourniquet sleeve 34 may have a right sleeve interior 37. As illustrated in FIG. 4, the left tourniquet sleeve 30 may have a left tourniquet retrieval opening 31 through which the tourniquet 62 (FIGS. 12-14) is retrievable from the left tourniquet sleeve 30. The left tourniquet retrieval opening 31 of the left tourniquet sleeve 30 may be adjacent to the first shell opening 9 at the first outer shell end 8 of die outer shell 2. As illustrated in FIG. 5, in some embodiments, the left tourniquet sleeve 30 may have a left sleeve end opening 32 opposite the lea tourniquet retrieval opening 31. In other embodiments, the left, tourniquet sleeve 30 may be closed-ended.

As further illustrated in FIG. 5, the right tourniquet sleeve 34 may have a right tourniquet retrieval opening 35 through which the tourniquet 62 (FIGS. 12-14) is retrievable from the right tourniquet sleeve 34. The right tourniquet retrieval opening 35 of the right tourniquet sleeve 34 may be adjacent to the second shell opening 11 at the second outer shell end 10 of the outer shell 2. Thus, the left tourniquet retrieval opening 31 of the left tourniquet sleeve 30 and the right tourniquet retrieval opening 35 of the right tourniquet sleeve 34 may be disposed at opposite ends of the outer shell 2. As illustrated in FIG. 4, in some embodiments, the right tourniquet sleeve 34 may have a right sleeve end opening 36 opposite the right tourniquet retrieval opening 35. In other embodiments, the right tourniquet sleeve 34 may be closed-ended.

As further illustrated in FIGS. 1-6, the left tourniquet sleeve 30 may have a left tourniquet strap 50 and the right tourniquet sleeve 34 may have a right tourniquet strap 60. The following description of each tourniquet strap 50, 60 will be described with respect to the right tourniquet strap 60 in the right tourniquet sleeve 34 in FIGS. 12-14. However, the same description may apply to the left tourniquet strap 50 of the left tourniquet sleeve 30.

Figure 12:
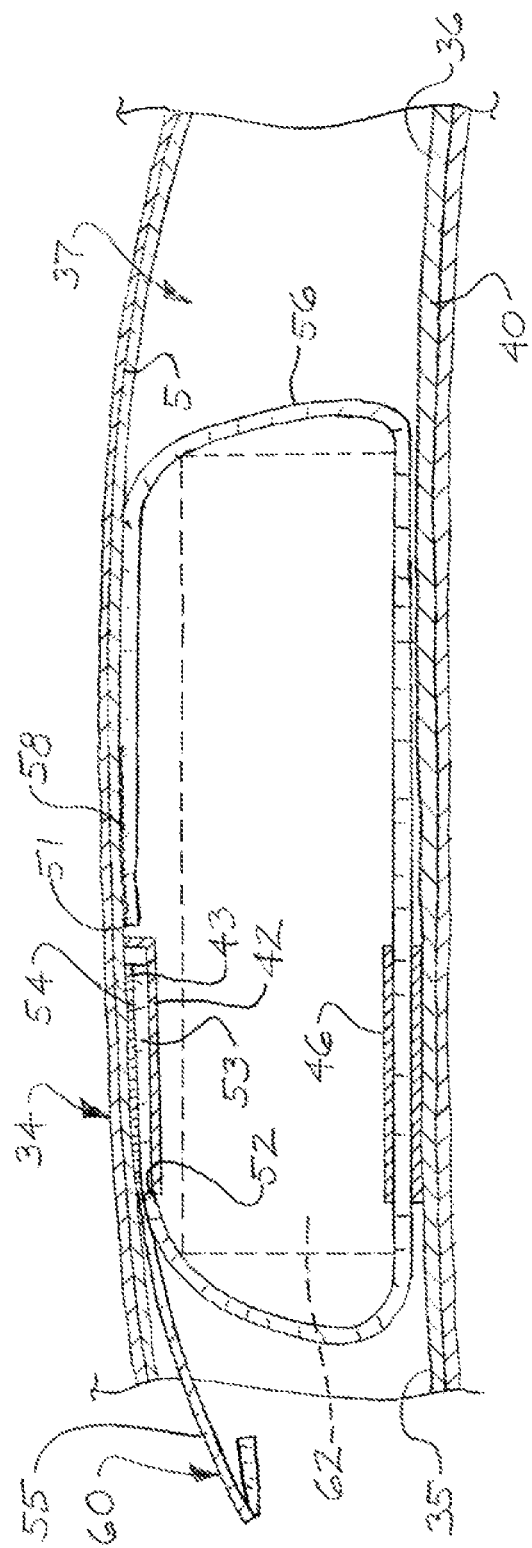
FIG. 12 is a longitudinal sectional view of a tourniquet sleeve in the outer shell of the illustrative IFAK package assembly, with a tourniquet (illustrated in phantom) deployed in place and a tourniquet strap in a retracted and secured position inside the tourniquet sleeve.
Figure 13:
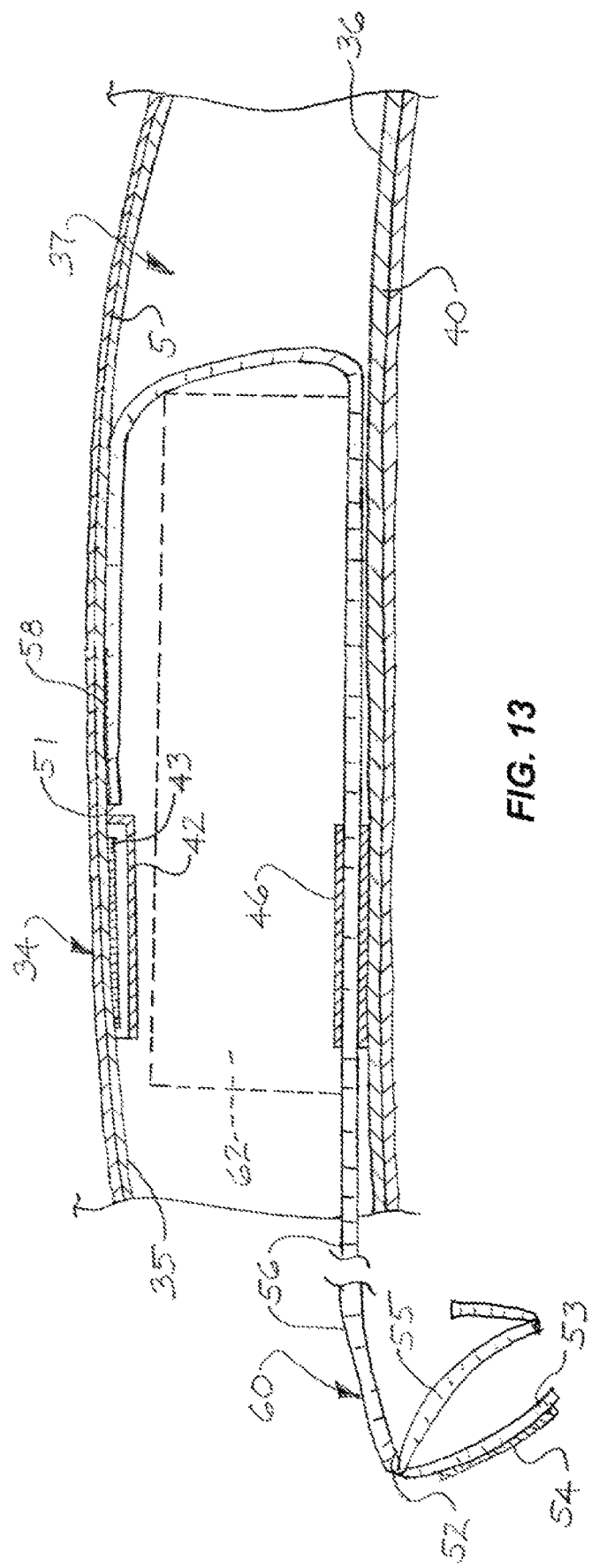
FIG. 13 is, a longitudinal sectional view of the tourniquet sleeve illustrated in FIG. 12, with the tourniquet strap unsecured and partially removed from the tourniquet sleeve to expose and initiate removal of the tourniquet from the tourniquet sleeve.
Figure 14:
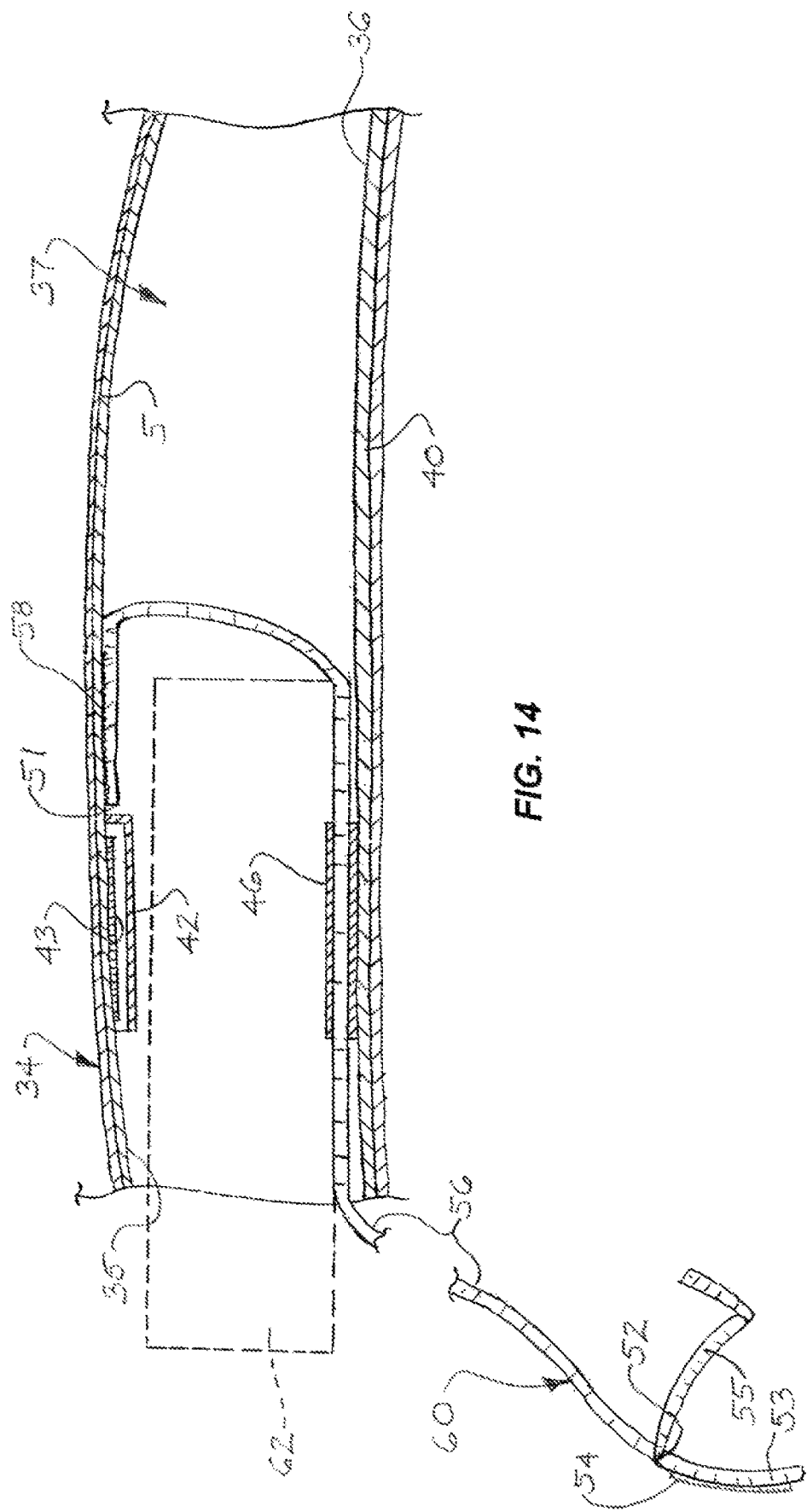
FIG. 14 is a longitudinal sectional view of the tourniquet sleeve illustrated in FIG. 12, with the unsecured tourniquet strap more fully removed from the tourniquet sleeve to push and partially protrude the tourniquet from the tourniquet sleeve for ease of access of the tourniquet on the part of a user.

As illustrated in FIGS. 12-14, a strap pocket 42 may be sewn or otherwise attached to the interior surface of the side outer shell wall 5 of the outer shell 2 inside the right sleeve interior 37 of the right tourniquet sleeve 34. The strap pocket 42 may be disposed nearer in proximity to the right tourniquet retrieval opening 35 than to the right sleeve end opening 36 of the right tourniquet sleeve 34. A interior attachment device 43 may be provided on the side outer shell wall 5 inside the strap pocket 42. The interior attachment device 43 may include a hook-and-loop-fastener and/or other type of mechanical fastener which is suitable for the purpose, the purpose of which will be hereinafter described.

As further illustrated in FIGS. 12-14, the right tourniquet strap 60 may include a main strap segment 36 having a strap attachment end 51 and a strap free end 52. A strap terminal segment 53 may extend from the strap free end 52. A strap attachment device 54 may be provided on the strap terminal segment 53 for detachable engagement with the interior attachment device 43 in the strap pocket 42. The strap attachment device 54 may be suitably configured to detachably engage the companion interior attachment device 43 in the strap pocket 42 for the purpose of detachably securing the strap terminal segment 53 inside the strap pocket 42 in the retracted position of the right tourniquet strap 60, as illustrated in FIG. 12. A strap tab 55 may extend from the strap free end 52 of the main strap segment 56 adjacent to the strap terminal segment 53.

The strap attachment end SI of the main strap segment 56 may be attached to the interior surface of the side outer shell wall 5 of the outer shell 2 inside the right sleeve interior 37, such as via strap stitching 58, for example and without limitation, at a location which is longitudinally between the strap pocket 42 and the right sleeve end opening 36 of the right tourniquet sleeve 34. In some embodiments, the strap attachment end 51 may be immediately adjacent to the strap pocket 42 toward the right sleeve end opening 36. Proceeding from the strap attachment end 51 to the strap free end 52, the main strap segment 56 may extend away from the strap stitching 58 initially toward the right sleeve end opening 36, then loop across the width of the right sleeve interior 37 and extend adjacent and parallel to the outer sleeve wall 40 toward the right tourniquet retrieval opening 35. As it extends along the outer sleeve wall 40, the main strap segment 56 may extend through a strap guide sleeve 46 which may be sewn or otherwise attached to the interior, surface of the outer sleeve wall 40.

In the retracted and secured position of the right tourniquet strap 60, illustrated in FIG. 12, the tourniquet 62 may be deployed in the right sleeve interior 37 with the main strap segment 56 surrounding or encircling the length of the tourniquet 62. The strap terminal segment 51 may be inserted and secured in the strap pocket 52 typically by attachment of the strap attachment device to the companion interior attachment device 43. Accordingly, the secured right tourniquet strap 60 prevents the tourniquet 62 from inadvertently falling from the right sleeve interior 37 through the right tourniquet retrieval opening 35 or the right sleeve end opening 36. As further illustrated in FIG. 12, the strap tab 55 may protrude from the right tourniquet retrieval opening 35 for ease of access to a user (not illustrated) of the assembly 1 in grasping the strap tab SS for subsequent retrieval of the tourniquet 62 from the right tourniquet sleeve 34, as will be hereinafter further described.

When use of the tourniquet 62 is needed, the user may grasp, and pull the protruding strap tab 55 away from the right tourniquet retrieval opening 35 to initially detach the strap attachment device 54 from the interior attachment device 43 and then remove the strap terminal segment 53 from the strap pocket 42. Thus, in the par fall removed positions of the right tow strap 60, illustrated in FIGS. 13 and 14, the tourniquet 62 may be exposed and the main strap segment 56 may protrude from the right sleeve interior 37 through the right tourniquet retrieval opening 35. As the user continues to pull the strap tab SS away from the right tourniquet retrieval opening 35, the interior looped portion of the main strap segment 56 may push the tourniquet 62 within the right sleeve interior 37 toward and ultimately from the right tourniquet retrieval opening 35, as illustrated in FIG. 14. Therefore, the user can then grasp and pull the exposed and protruding tourniquet 62 front the right sleeve interior 37 for use of the tourniquet 62. It will be appreciated by those skilled in the art that the secured and retracted right tourniquet strap 56b (FIG. 12) renders the tourniquet 62 readily accessible while preventing the tourniquet 62 from inadvertently falling from the right sleeve interior 37 of the right tourniquet sleeve 34 when access is not desired or needed.

As illustrated in FIG. 1, in some embodiments, multiple, adjacent front compression straps 14 may extend transversely across the front outer shell wall 4 of the outer shell 2 between the left tourniquet sleeve 30 and the right tourniquet sleeve 34. A hook and loop fastener 15 may be provided on at least one of the front compression straps 14. As illustrated in FIG. 3, rear compression straps may include multiple MOLLE straps 23 and multiple belt loop straps 24 which may in like manner extend transversely across the rear outer shell wall 4 of, the outer shell 2 between the left tourniquet sleeve 30 and the right tourniquet sleeve 34. The MOLLE straps 23 may facilitate mounting of the assembly 1 on MOLLE, whereas the belt loop straps 24 may facilitate mounting of the assembly 1 on, a belt (not illustrated) which may be worn by the user. In some embodiments, a pair of the MOLLE straps 23 may be disposed at the first outer shell end 8 and the second outer shell end 10, respectively, of the outer shell 2, as illustrated. A pair of the belt loop straps 24 may be disposed on the insides of the respective outer MOLLE straps 23. An additional pair of the MOLLE straps 23 may be disposed at the center of the outer shell 2 between the belt loop straps 24. In alternative embodiments, the outer shell 2 may be fitted with any number of the MOLLE straps 23 and the belt loop straps 24 inane desired sequence or arrangement.

Figure 6:
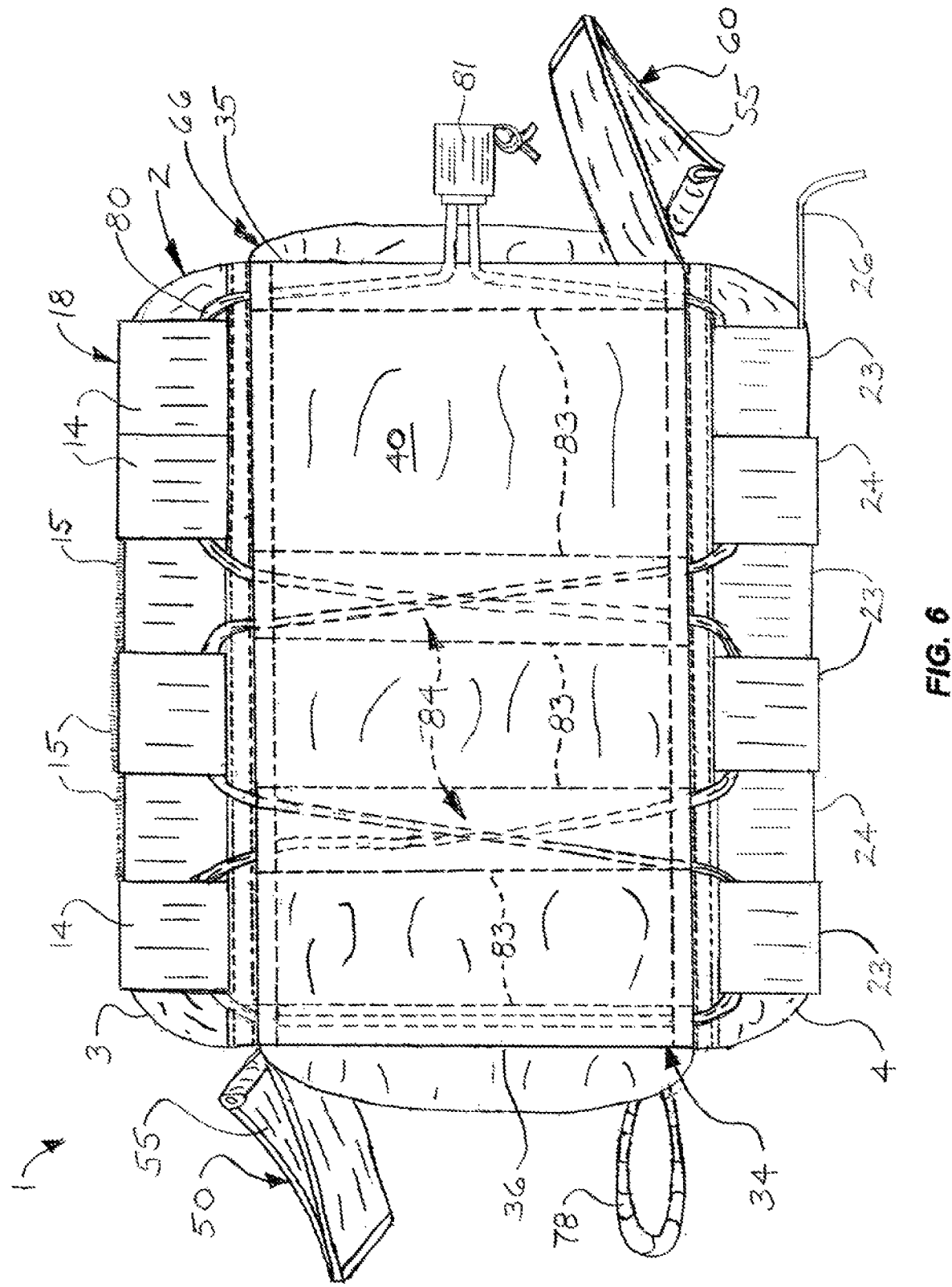
FIG. 6 is a right side view of an illustrative IFAK package assembly, more particularly illustrating, a typical configuration of a sleeve compression cord (illustrated in phantom) in each tourniquet sleeve.

As illustrated in FIGS. 1, 3 and 6, an elastic sleeve compression cord 80 may be sandwiched between adjacent inner and outer layers (not illustrated) of the outer sleeve wall 40 of each of the left tourniquet sleeve 30 and the right tourniquet sleeve 34. As illustrated in FIG. 6, each sleeve compression cord 80 may extend through the looped ends of the front compression straps 14 and the MOLLE straps 23 and belt loop straps 24 on the side of the outer shell 2 of the corresponding left tourniquet sleeve 30 and right tourniquet sleeve 34. As further illustrated in FIG. 6, stitching 83 may attach the inner and outer layers of the outer sleeve wall 40 to each other to form cord channels 84 between the layers and within which the sandwiched compression cord 80 extends. Accordingly, in some embodiments, each sleeve compression cord 80 may repeatedly traverse the width of the corresponding left tourniquet sleeve 30 or right tourniquet sleeve 34 in a winding or crisscrossing pattern to normally exert a pulling force which draws the front compression straps 14 and MOLLE straps 23 and belt loop straps 24 toward each other across the width of and inwardly against the outer shell 2. The compression cords 80 may additionally exert an inward pulling force on the respective left tourniquet sleeve 30 and right tourniquet sleeve 34. Thus, the inward compression force applied by the front compression straps 14, the MOLLE straps 23, the belt loop straps 24 and the sleeve compression cords 80 may maintain the tourniquets 62 securely in place in the respective left sleeve interior 33 of the left tourniquet sleeve 30 and the right sleeve interior 37 of the right tourniquet sleeve 34 as well as maintain the interior sleeve 66 securely in place in the outer shell interior 6 of the outer shell 2. As illustrated in FIGS. 4 and 5, the inward compression force which is applied by, the front compression straps 14, the straps 23, the belt loop straps 24 and the sleeve compression cords 80 may partially collapse the left tourniquet sleeve 30, the right tourniquet sleeve 34 and the outer shell 2 when the tourniquets 62 are removed from the respective left tourniquet sleeve 30 and right tourniquet sleeve 34 and the interior sleeve 66 is removed from the outer shell 2.

As further illustrated in FIG. 6, in some embodiments, the ends of each sleeve compression cord 80 may extend through a typically adjustable, spring-loaded, button-actuated cord stay 81 to facilitate selective adjustment in the tension which the sleeve compression cord 80 applies to the front compression straps 14, the MOLLE straps 23 and the belt loop straps 24. Accordingly, the spring-loaded cord stay button (not illustrated) on the cord stay 81 may be depressed, the sleeve compression cord 80 tensioned and pulled through the cord stay 81 and the cord stay button released to lock the tensioned sleeve compression cord 80. Tensioning of the sleeve compression cord 80 may prevent the interior sleeve 66 from shifting in the outer shell interior 6 of the outer shell 2 in the event that the tourniquets 62 are removed from the respective left tourniquet sleeve 30 and right tourniquet sleeve 34.

As further illustrated in FIG. 1, in some embodiments, the front compression straps 14 may form a trauma shear sleeve 18 between the exterior surface of the front outer shell wall 3 of the outer shell 2 and the front compression straps 14. Accordingly, a pair of trauma shears 78 may be inserted in the trauma shear sleeve 18 for stowage. A securable shear securing strap 20 may be provided on the front outer sleeve wall 3 to additionally secure the trauma shears 78 in place.

As illustrated in FIG. 3, in some embodiments, a pair of assembly mount straps 26 may be sewn and/or otherwise attached to the rear inner shell wall 4 of the outer shell 2. The assembly mount straps 26 may generally extend the length of the outer shell 2 typically between the MOLLE straps 23 and the belt loop straps 24 and the outer surface of the rear inner shell wall 4. The MOLLE straps 23, belt loop straps 24 and assembly mount straps 26 may facilitate horizontal or vertical mounting of the outer shell 2 on MOLLE or on a belt (not illustrated) which may be worn by law enforcement or military personnel in typical application of the assembly 1. In some embodiments, buttons (not illustrated), hook and loop fasteners and/or other strap attachment device 25 may be provided on the assembly mount straps 26 for fastening purposes.

Referring next to FIGS. 7-11 of the drawings, the interior sleeve 66 of the assembly 1 may facilitate securement of various first aid items 88, 90 (FIG. 8) in the outer shell 2. The interior sleeve 66 may be fabricated of a multi-layered, flexible and durable fabric material or materials. The interior sleeve 66 may be selectively deployable in an extended configuration (FIGS. 7 and 8) which facilitates access of the user to the first aid items 88, 90, or in a folded configuration (FIGS. 9-11) which facilitates compact placement of the interior sleeve 67 in the outer shell interior 6 of the outer shell 2, as illustrated in FIGS. 1-3. The interior sleeve 66 may have an exterior sleeve surface 92 (FIG. 7) and an interior sleeve surface 93 (FIG. 8).

As illustrated in FIG. 8, in some embodiments, the interior sleeve 66 may include a first sleeve section 67, a second sleeve section 70, a third sleeve section 73 and a fourth sleeve section 85 on the interior sleeve surface 93. The first sleeve section 67 may be suitably sized and configured to accommodate various first aid items 88. Multiple first section securing straps 68 may extend across the width of the interior sleeve 66 at the first sleeve section 67 to secure the first aid items 88 on the interior sleeve 66. In some non-limiting embodiments, the first aid items 88 may include a nasopharyngeal airway (NPA) with lube, a Hyfin-type chest seal twin pack, two decompression needles with catheter (14 ga×3.25 in), a black marking permanent pen and a TCCC casualty card, for example and without limitation.

Figure 15:
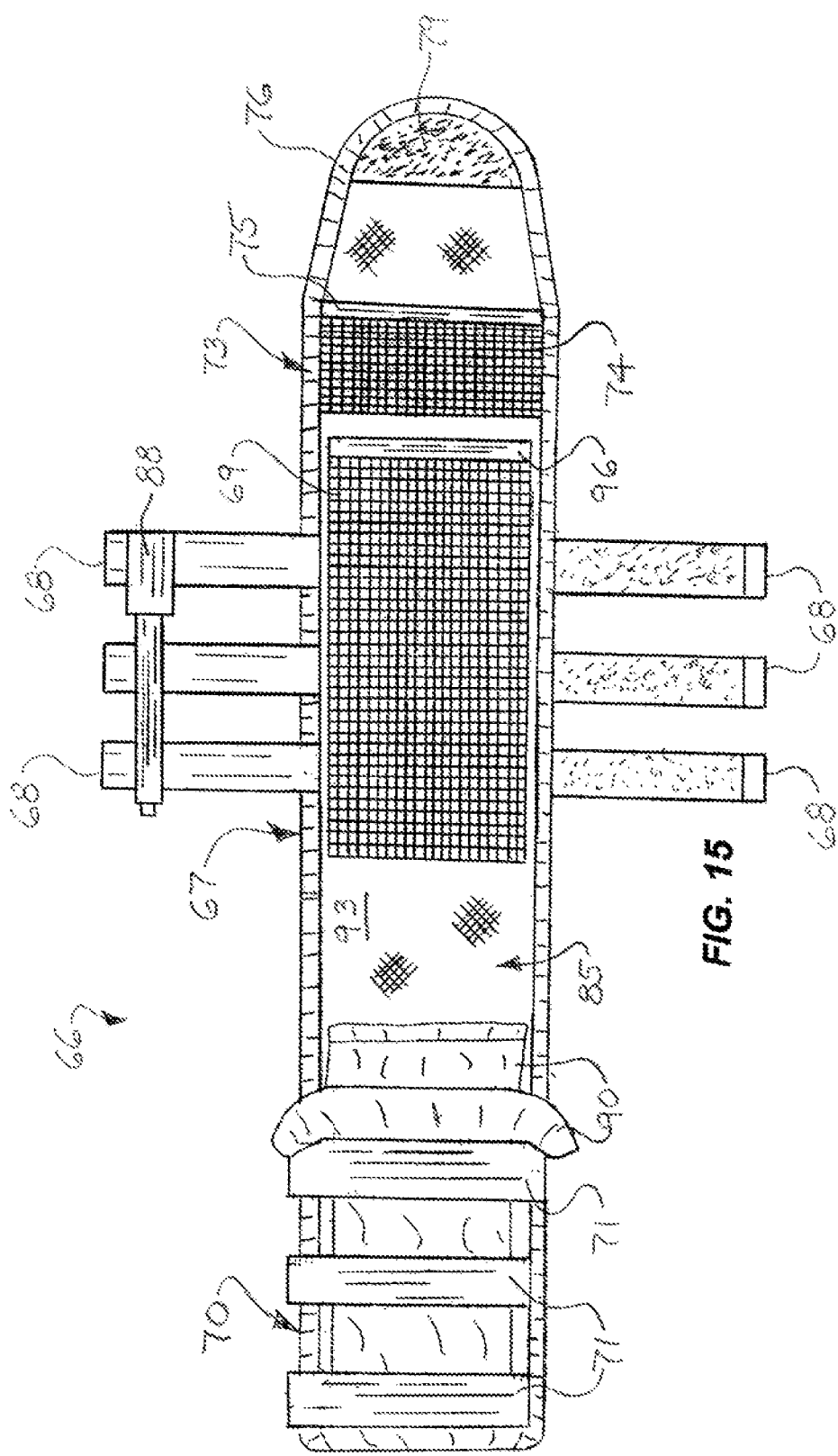
FIG. 15 is an interior view of the illustrative interior sleeve of the IFAK package assembly illustrated in FIG. 7, deployed in the extended configuration, with multiple securing straps in an unsecured position to expose a mesh pocket on the interior sleeve.

As illustrated in FIG. 15, in some embodiments, the first sleeve section 67 of the interior sleeve 66 may include a mesh pocket 69 having a retaining band % at the opening thereof. The mesh pocket 69 may underlie the first section securing straps 68. Accordingly, in some applications, the mesh pocket 69 may be used to secure a TCCC card and a black marking permanent pen (not illustrated), for example and without limitation.

The second sleeve section 70 of the interior sleeve 66 may be suitably sized and configured to accommodate various first aid items 90. Multiple second section securing straps 71 may extend across the width of the interior sleeve 66 at the second sleeve section 70 to secure the first aid items 90 on the interior sleeve 66. In some non-limiting embodiments, the first aid items 90 may include an elastic ACE® bandage with VELCRO® (6 in×5.3 ft.), non-sterile; hemostatic gauze (QUICKCLOT® or CHITOGAUZE®); and vacuum-packed S-rolled gauze, for example and without limitation.

The third sleeve section 73 of the interior sleeve 66 may include a mesh pocket 74 which may be secured to the interior sleeve surface 93 of the interior sleeve 66 according to the knowledge of those skilled in the art. A retaining band 75 may be provided at the opening of the mesh pocket 74. In some applications, a combat pill pack (not illustrated) may be placed in the mesh pocket 74 for potential use.

The fourth sleeve section 85 of the interior sleeve 66 may be disposed between the first sleeve section 67 and the second sleeve section 70. In some embodiments, the fourth sleeve section 85 may be fitted with a securing strap (not illustrated), pocket (not illustrated) and/or other storage or securing device to facilitate stowage of additional first aid items.

Figure 7:
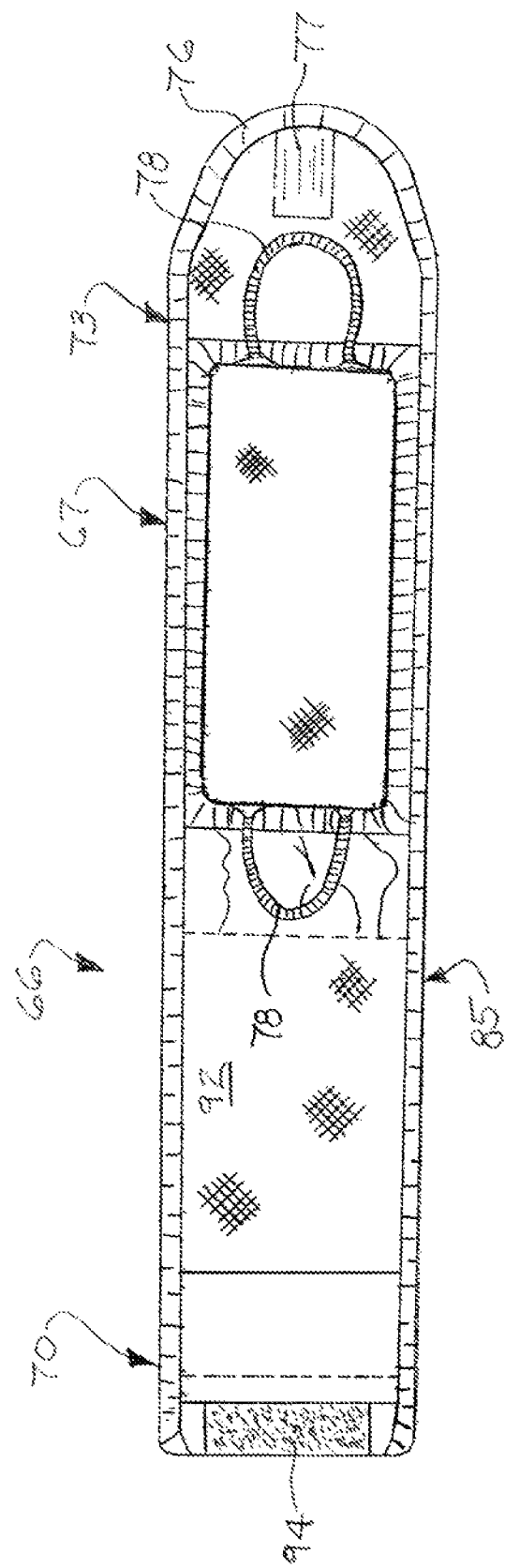
FIG. 7 is an exterior view of an illustrative interior sleeve of the IFAK package assembly, deployed in an extended configuration.
Figure 9:
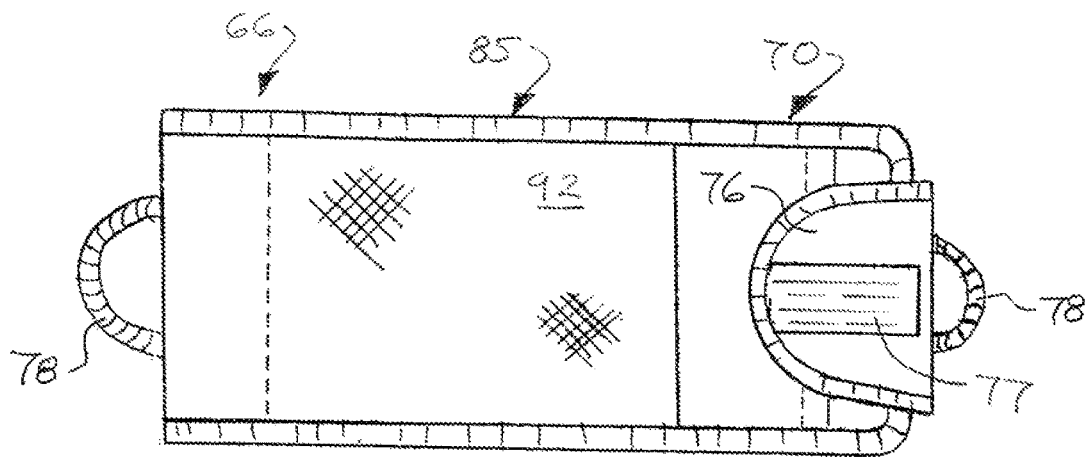
FIG. 9 is a front view of the illustrative interior sleeve, deployed in, a folded configuration.
Figure 10:
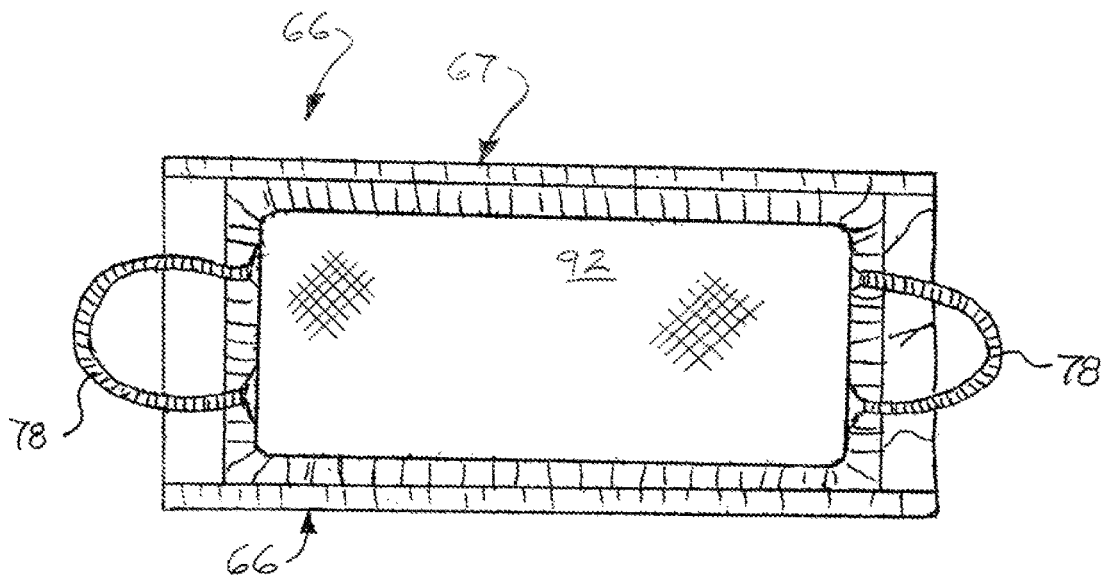
FIG. 10 is a rear view of the illustrative interior sleeve deployed in the folded configuration.

As illustrated in FIGS. 7 and 8, a sleeve tab 76 may terminate a first end of the interior sleeve 66. A sleeve tab fastener 79 (FIG. 8) may be provided on the sleeve tab 76 on the interior sleeve surface 93 of the interior sleeve 66. A companion sleeve fastener 94 (FIG. 7) may be provided at a second end of the interior sleeve 66 on the exterior sleeve surface 92. Accordingly, as illustrated in FIGS. 9-11, the interior sleeve 66 can be selectively deployed in die folded configuration by folding the first sleeve section 67, the second sleeve section 70, the third sleeve section 73 and the fourth sleeve section 85 with respect to each other and secured by engagement of the sleeve tab fastener 79 with the companion sleeve fastener 94. As illustrated in FIGS. 7 and 11, a sleeve tab loop 77 may be provided on the sleeve tab 76 on the exterior sleeve surface 92 to facilitate manual disengagement of the sleeve tab fastener 79 from the sleeve fastener 94 for deployment of the interior sleeve 66 in the extended configuration. In some embodiments, an elastic material (not illustrated) may attach the sleeve tab loop 77 to the sleeve tab fastener 76.

As illustrated in FIGS. 7 and 10, in some embodiments, a pair of sleeve handle loops 78 may extend from opposite ends of the first sleeve section 67 on the exterior sleeve surface 92 of the interior sleeve 66. Accordingly, when the folded interior sleeve 66 is deployed in place in the outer shell interior 6 of the outer shell 2, as illustrated in FIG. 1, the sleeve handle loops 78 may extend from the respective first shell opening 9 and second shell opening 11 at the first outer shell end 8 and the second outer shell end 10, respectively, of the outer shell 2. Thus, a left-handed or right-handed user can ambidextrously grasp a selected one of the sleeve handle loops 78 and pull the interior sleeve 66 from the outer shell 2, as illustrated in FIG. 3, irrespective of the side of the user on which the assembly 1 is mounted, in order to expeditiously access the first aid items 88, 90 (FIG. 8) in the interior sleeve 66.

In typical application of the assembly 1, the interior sleeve 66 may be removed from the outer shell interior 6 of the outer shell 2 and unfolded and deployed in the extended configuration illustrated in FIG. 8, Me first aid items 88, 90 may be secured in the interior sleeve 65, typically as was heretofore described with respect to FIG. 8. The interior sleeve 66 may be folded and placed back into the outer shell interior 6 with the sleeve handle loops 78 typically protruding from the first shell opening 9 and the second shell opening 11 at the respective first outer shell end 8 and second outer shell end 10 of the outer shell 2, as illustrated in FIG. 1.

A tourniquet 62 may be placed in the right sleeve interior 37 of the right tourniquet sleeve 34. As illustrated in FIG. 12, the main strap segment 56 of the right tourniquet strap 60 may surround or encircle the length of the tourniquet 62. The strap terminal segment 53 on the right tourniquet strap 60 may then be inserted in the strap pocket 42 in the left sleeve interior 33, and the strap attachment device 54 on the strap terminal segment 53 attached to the companion interior attachment device 43 in the strap pocket 42. Accordingly, as further illustrated in FIG. 12, the main strap segment 56 may surround or encircle the length of the tourniquet 62 to prevent the tourniquet 62 from inadvertently falling from the corresponding left sleeve interior 33 or right sleeve interior 37. The same procedure may be carried out with respect to the left tourniquet sleeve 30. The strap tab 55 on the corresponding left tourniquet strap 50 and right tourniquet strap 60 may protrude from the respective left tourniquet retrieval opening 31 of the left tourniquet sleeve 30 and the right tourniquet retrieval opening 35 of the right tourniquet sleeve 34, as shown, for ease of access to the user of the assembly 1. A pair of trauma shears 22 may be placed in the trauma shear sleeve 18 and secured via the shear securing strap 20, as illustrated in FIG. 1. MOLLE straps 23, the belt loop straps 24 and/or the assembly mount straps 26 (FIG. 3) may facilitate horizontal or vertical mounting of the assembly I on or on a belt (not illustrated) which may be worn by law enforcement personnel, military personnel or other user.

In the event that use of a tourniquet 62 is required, the user may retrieve the tourniquet 62 in the left tourniquet sleeve 30 or the tourniquet 62 in the right tourniquet sleeve 34 depending on ease of access and typically on whether the user is left-handed or right-handed and the side of the user's body on which, the assembly 1 is mounted. Accordingly, the user may grasp and pull the protruding strap tab 55 of the corresponding left tourniquet strap 50 or right tourniquet strap 60 away from the left tourniquet sleeve 30 or right tourniquet sleeve 34. This action detaches the strap attachment device 54 on the strap terminal segment 53 from the interior attachment device 43 in the strap pocket 42 and exposes the tourniquet 62 through the corresponding left tourniquet retrieval opening 31 or right tourniquet retrieval opening 35, as illustrated in 13. Continued pulling of the strap tab 55 causes the main strap segment 56 to push the tourniquet 62 within the left sleeve interior 33 or right sleeve interior 37 typically until the tourniquet 62 protrudes from the left tourniquet retrieval opening 31 or right tourniquet retrieval opening 35, as illustrated in FIG. 14. The user may then grasp and pull the tourniquet 62 from the left tourniquet sleeve 30 or right tourniquet sleeve 34 for use.

In the event that one of the first aid items 88, 90 is required, the user may retrieve the interior sleeve 66 from the outer shell 2. Accordingly, the user may grasp and pull the sleeve handle loop 78 at the first outer shell end 8 or the second, outer shell end 10 of the outer shell 2 depending on ease of access and typically on whether the user is left-handed or right-banded and the side of the user's body on which the assembly 1 is mounted. The user may then pull the outer shell 2 from the outer shell interior 6, as illustrated in FIG. 3. The user may unfold the initially folded interior sleeve 66 to the extended configuration, as illustrated in FIG. 8, and retrieve one or more of the first aid items 88, 90 for use. In the event that gauze or other one of the first aid items 88, 90 requires cutting, the user may release the shear securing strap 20 and retrieve the trauma shears 22 from the trauma shear sleeve 18 for the purpose.

After use, the tourniquet 62 may be replaced in the left tourniquet sleeve 30 or right tourniquet sleeve 34. The first, aid items 88, 90 which were used may be replaced in the interior sleeve 66. The interior sleeve 66 may be folded and replaced in the outer shell interior 6 of the outer shell 2.

Referring next to FIGS. 16-27 of the drawings, an alternative illustrative embodiment of the IFAK package assemblies is generally indicated by reference numeral 101. In the IFAK package assembly 101, elements which are analogous to the respective elements of the IFAK package assembly 1 that was heretofore described with respect to FIGS. 1-15 are designated by the same respective numerals in the 101-199 series in FIGS. 16-27, unless otherwise noted.

Figure 24:
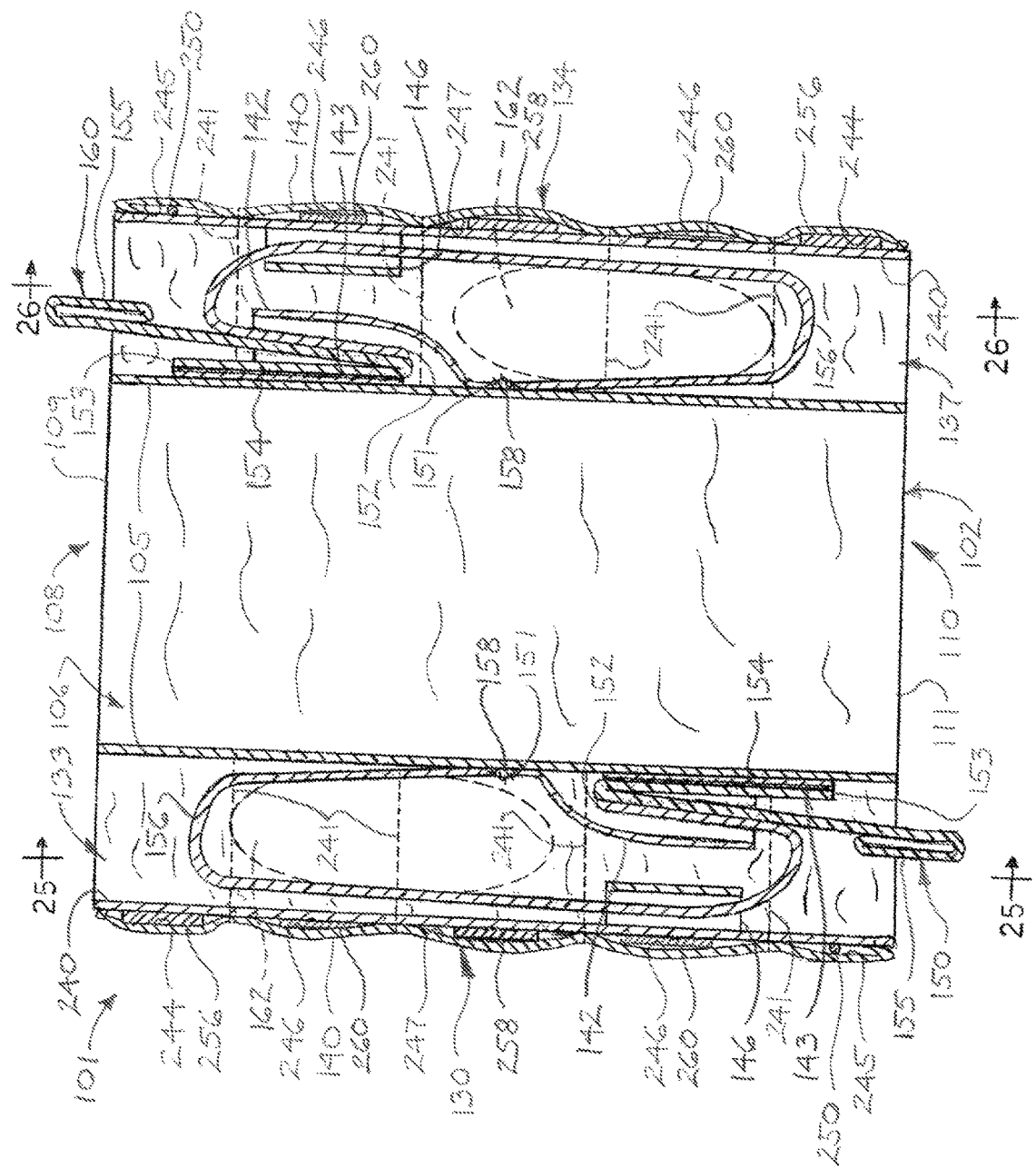
FIG. 24 is a longitudinal sectional view of the outer shell and left and right tourniquet sleeves of the IFAK package assembly, with the interior sleeve removed from the outer shell.
Figure 25:
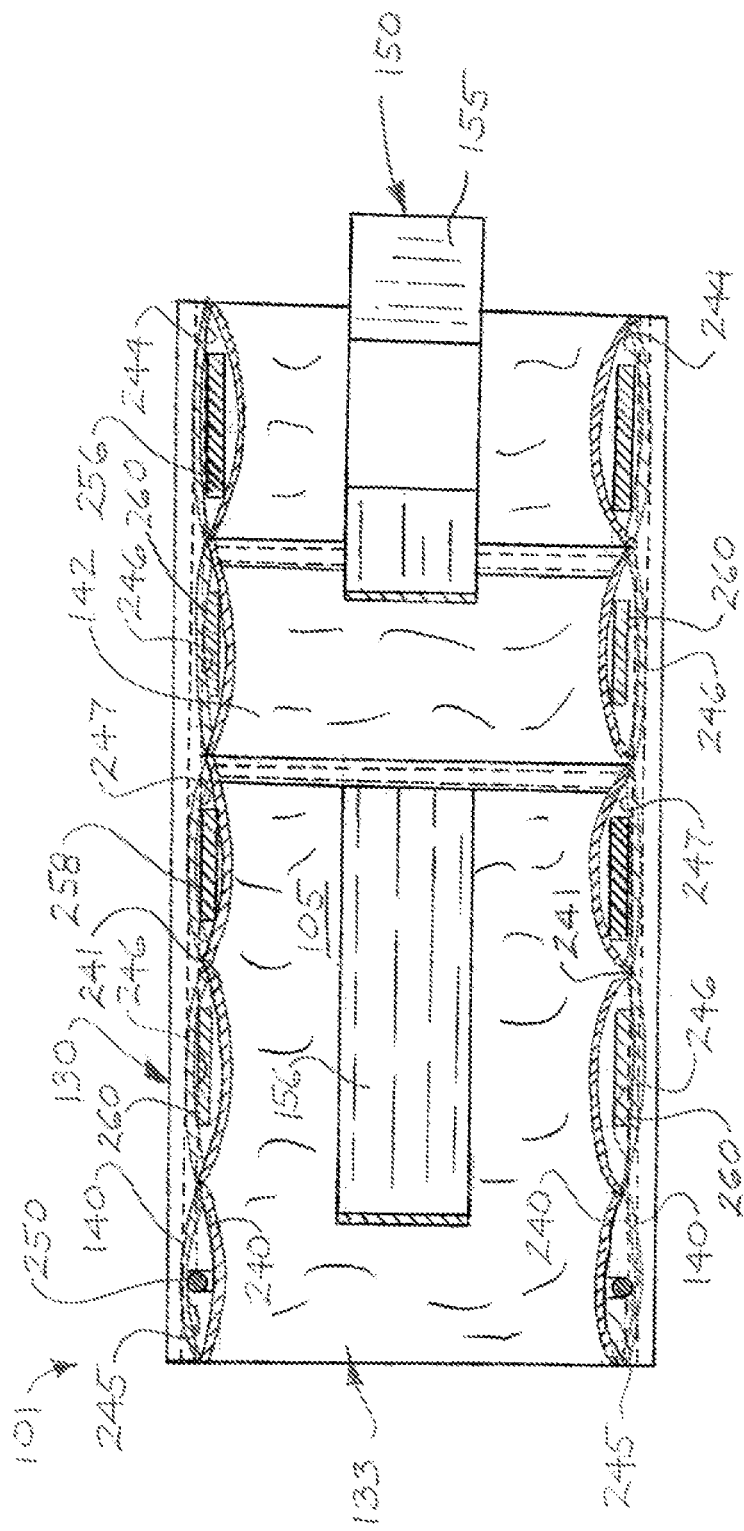
FIG. 25 is a sectional view, taken along section lines 25-25 in FIG. 24, of the left tourniquet sleeve.
Figure 26:
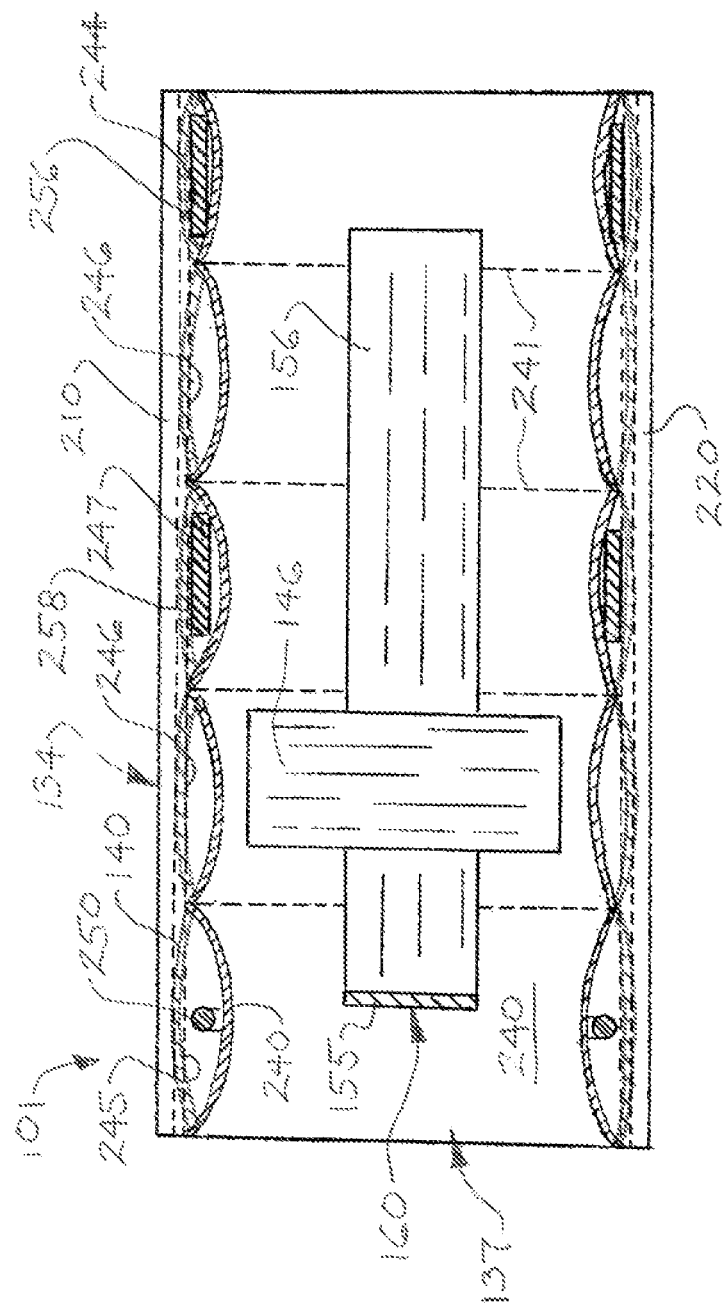
FIG. 26 is a sectional view, taken along section lines 26-26 in FIG. 24, of the right tourniquet sleeve.

As illustrated in FIGS. 24-26, in some embodiments, each of the left tourniquet sleeve 130 and the right tourniquet sleeve 134 of the IFAK package assembly 101 may include at least one inner sleeve layer 240. The inner sleeve layer 240 may have front and rear inner sleeve layer side edges (not illustrated) which may be sewn or stitched to the respective front outer shell wall 103 and rear outer shell wall 104 (FIG. 20) of the outer shell 102 via a respective pair of front seams 210 (FIG. 16) and rear seams 220 (FIG. 17), respectively. The pair of front seams 210 and the pair of rear seams 220 may be extend in parallel, spaced-apart relationship with respect to each other along the respective opposite side edges of the corresponding front outer shell wall 103 and rear outer shell wall 104. Accordingly, the left sleeve interior 133 and the right sleeve interior 137 may be formed by and between each side outer shell wall 105 of the outer shell 102 and the outer sleeve wall 240 of each corresponding left tourniquet frame 130 and right tourniquet sleeve 134.

Figure 20:
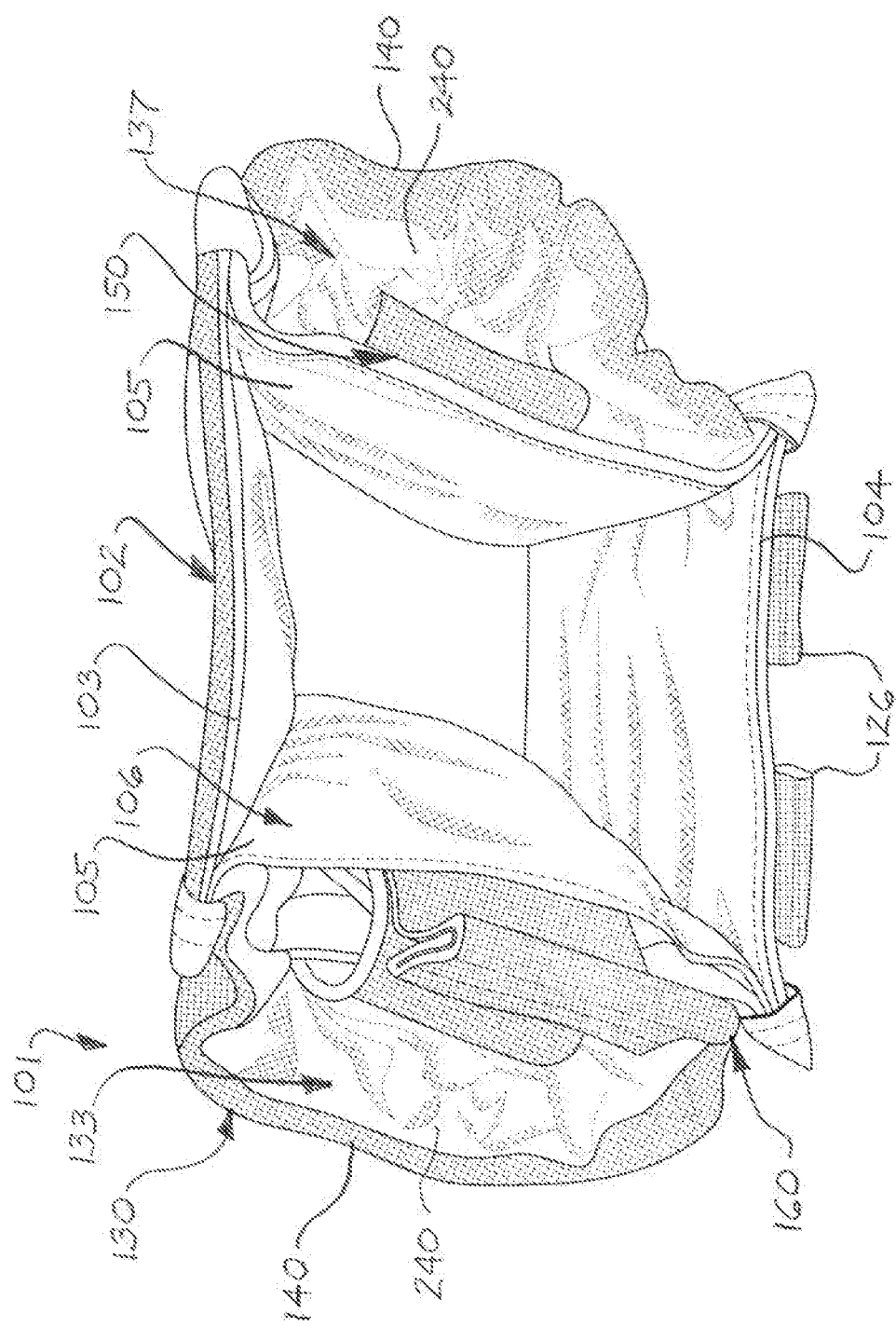
FIG. 20 is a front view of the illustrative IFAK package assembly illustrated in FIG. 16, with the interior sleeve removed from the outer shell.
Figure 21:
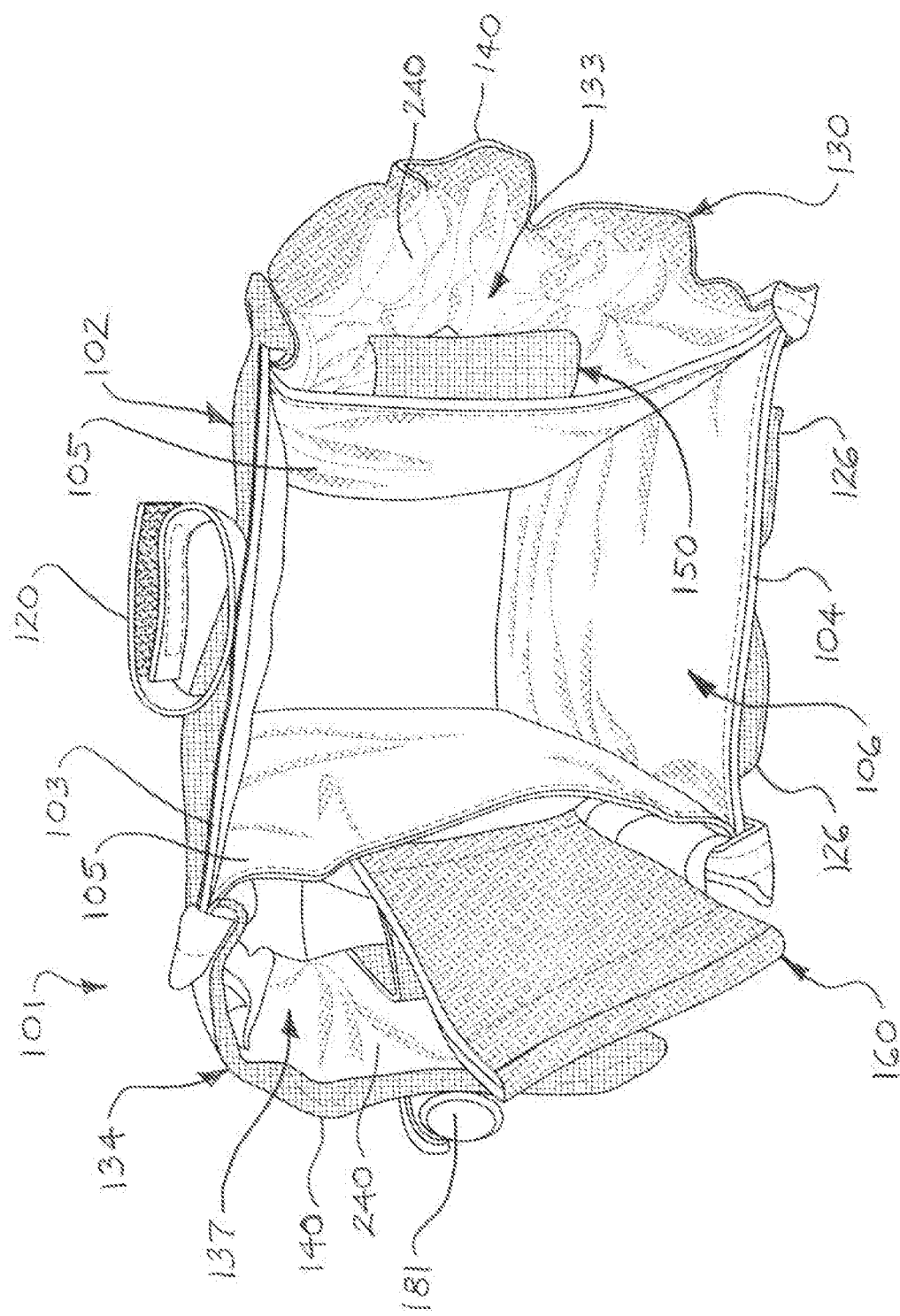
FIG. 21 is a rear view of the illustrative IFAK package assembly illustrated in FIG. 16, with the interior sleeve removed from the outer shell.

At least one outer sleeve wall 140 may be disposed outside of and adjacent to each corresponding inner sleeve layer 240. Like the inner sleeve layer 240, the outer Sleeve wall 140 may have front and rear outer sleeve wall edges (not illustrated) which may be sewn, stitched and/or otherwise attached to the respective front outer shell wall 103 and rear outer shell 104 of the outer shell 102 via the respective front seams 210 and rear seams 220 respectively. Accordingly, as illustrated in FIGS. 20 and 21, each inner sleeve layer 240 and outer sleeve wall 140 may be generally semicircular in end view or cross-section.

As further illustrated in FIGS. 24-26, a first terminal sleeve 44 and a second terminal sleeve loop 245 may be formed by and between the inner sleeve layer 240 and the outer sleeve wall 140 of each corresponding left tourniquet sleeve 130 and right tourniquet sleeve 134. A pair of intermediate sleeve loops 246 may be formed by and between the inner sleeve layer 240 and the outer sleeve wall on the insides of the respective first terminal sleeve loop 244 and second terminal Sleeve loop 245. A center sleeve loop 247 may be formed by and between the inner sleeve layer 240 and the outer sleeve wall 140 between the intermediate sleeve loops 246. Accordingly, the first terminal sleeve loop 244, second terminal sleeve loop 245, intermediate sleeve loops 246 and center sleeve loop 247 may extend across the semicircular width of each inner sleeve layer 240 and corresponding out sleeve wall 140. Sleeve stitching 241 may attach the outer sleeve wall 140 to the inner sleeve layer 240 between the adjacent first terminal sleeve loop 244 second terminal sleeve loop 245, intermediate sleeve loops 246 and center sleeve loop 247.

At least one terminal sleeve compression band 256 may extend through the first terminal sleeve loop 244. At least one center sleeve compression band 258 may in like manner extend through the center sleeve loop 247. In some embodiments, at least one intermediate sleeve compression band 260 may extend through each intermediate sleeve loop 246. At least one sleeve compression cord 250, selectively securable via cord stay 251, may extend through the second terminal sleeve loop 245. Accordingly, the terminal sleeve compression band 256, the center sleeve compression band 258, intermediate sleeve compression hand or bands 260 and the sleeve compression cord 250 may apply at least partial circumferential compression forces to the left tourniquet sleeve 130 and the right tourniquet sleeve 134.

In some embodiments, the outer sleeve wall 140 and/or the inner sleeve layer 240 of each of the left tourniquet sleeve 130 and the right tourniquet sleeve may include a stretchy, elastic or resilient material such as mesh, for example and without limitation. Accordingly, the outer sleeve wall 140 or the inner sleeve layer 240 may be omitted. In some embodiments, the Sleeve compression cords 250 may be omitted. The terminal sleeve compression band 256, center sleeve compression hand 258 and/or any other compression band or bands and/or the mesh or other stretchy, elastic or resilient material of which the left tourniquet sleeve 130 and right tourniquet sleeve 134 is made may apply and maintain sufficient inward elastic compression of the left tourniquet sleeve 130 and the right tourniquet sleeve 134 into the left sleeve interior 133 and the right sleeve interior 137, respectively, to sufficiently retain the tourniquet 162 in the corresponding left tourniquet sleeve 130 and right tourniquet sleeve 134 until retrieval typically by pulling of the respective left tourniquet strap 150 and right tourniquet strap 160.

Figure 16:
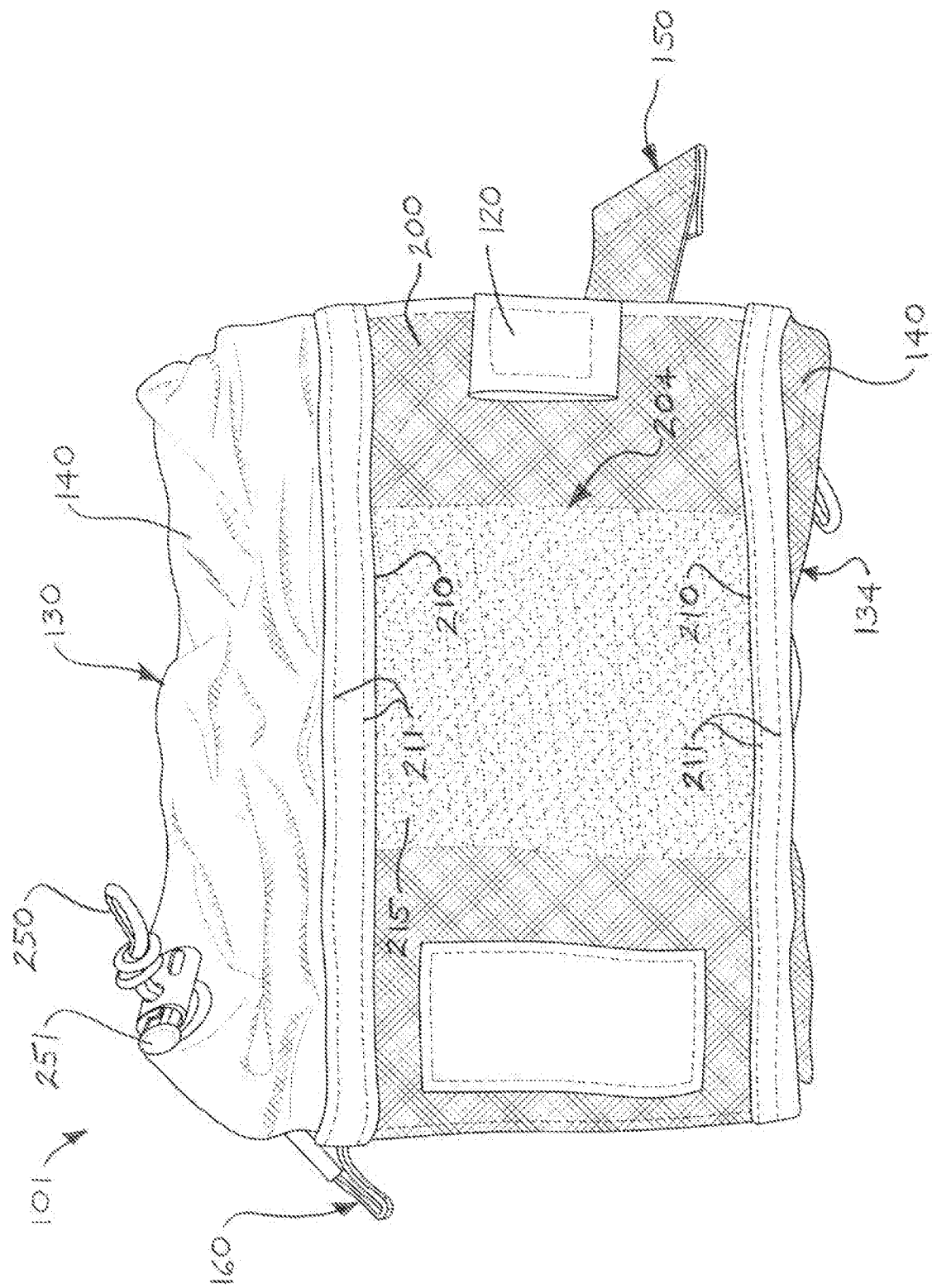
FIG. 16 is a top view of an alternative illustrative embodiment of the IFAK package assemblies.
Figure 17:
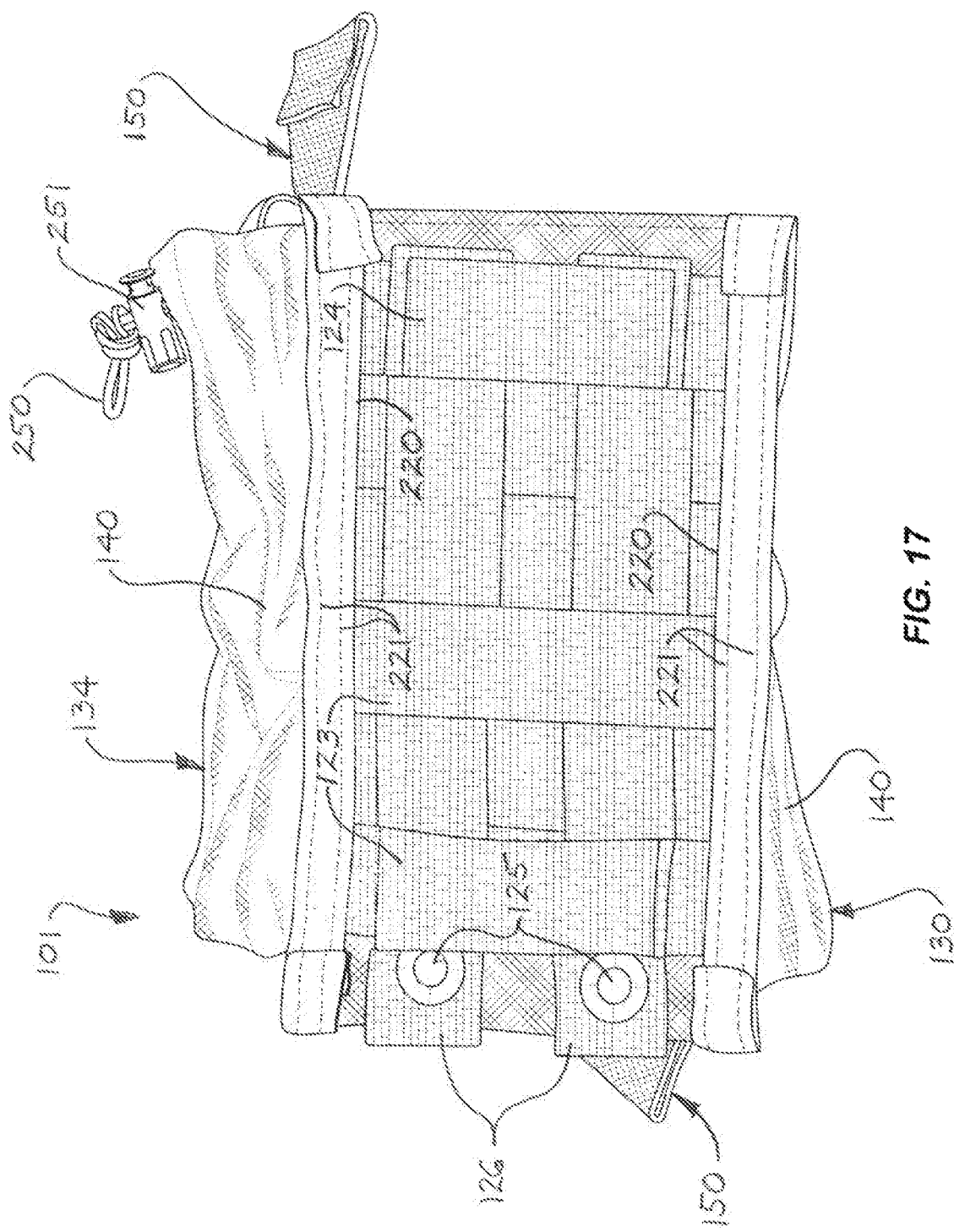
FIG. 17 is a bottom view of the illustrative IFAK package assembly illustrated in FIG. 16.
Figure 18:
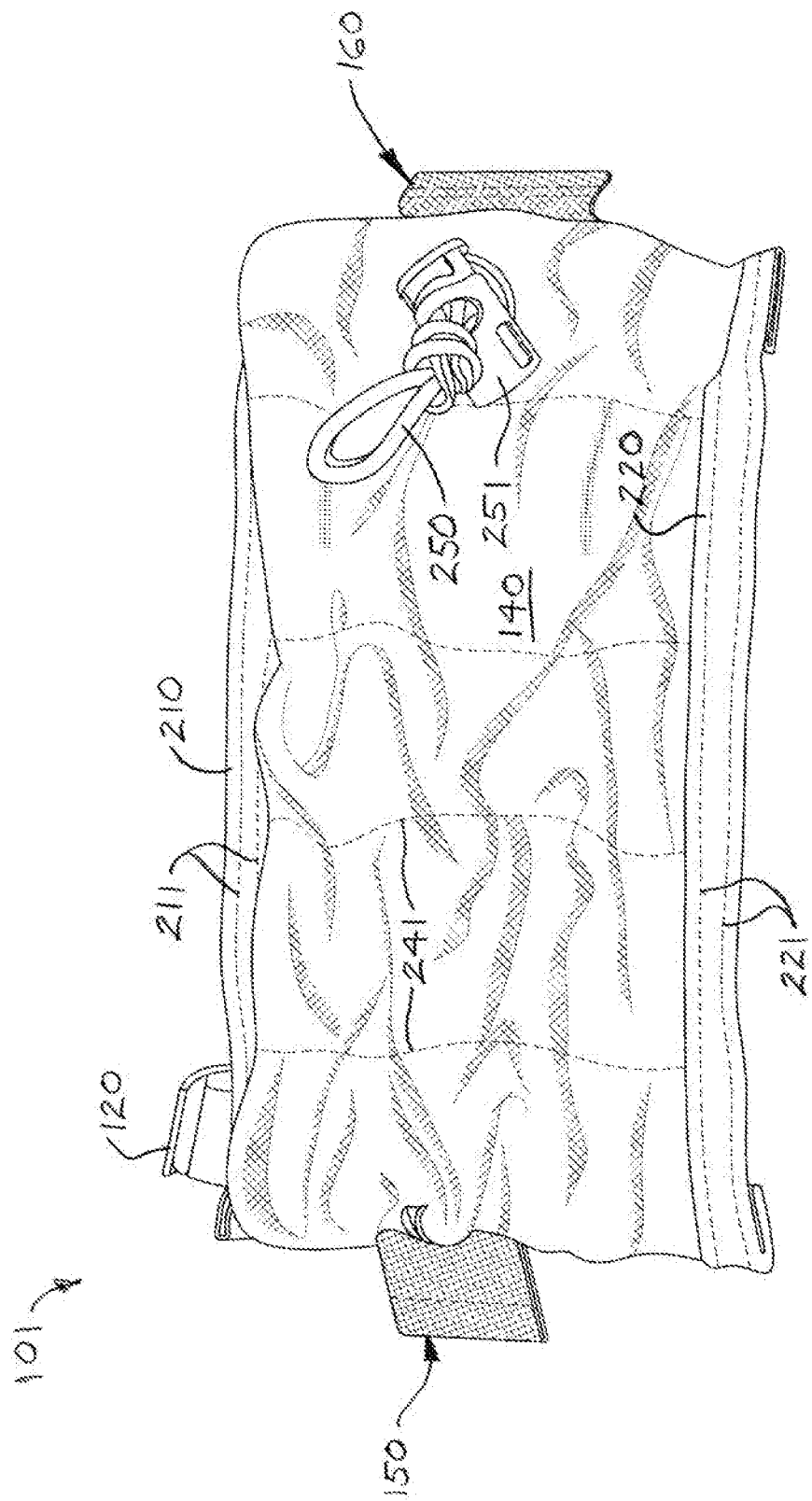
FIG. 18 is a left side of the illustrative IFAK package assembly illustrated in FIG. 16.
Figure 19:
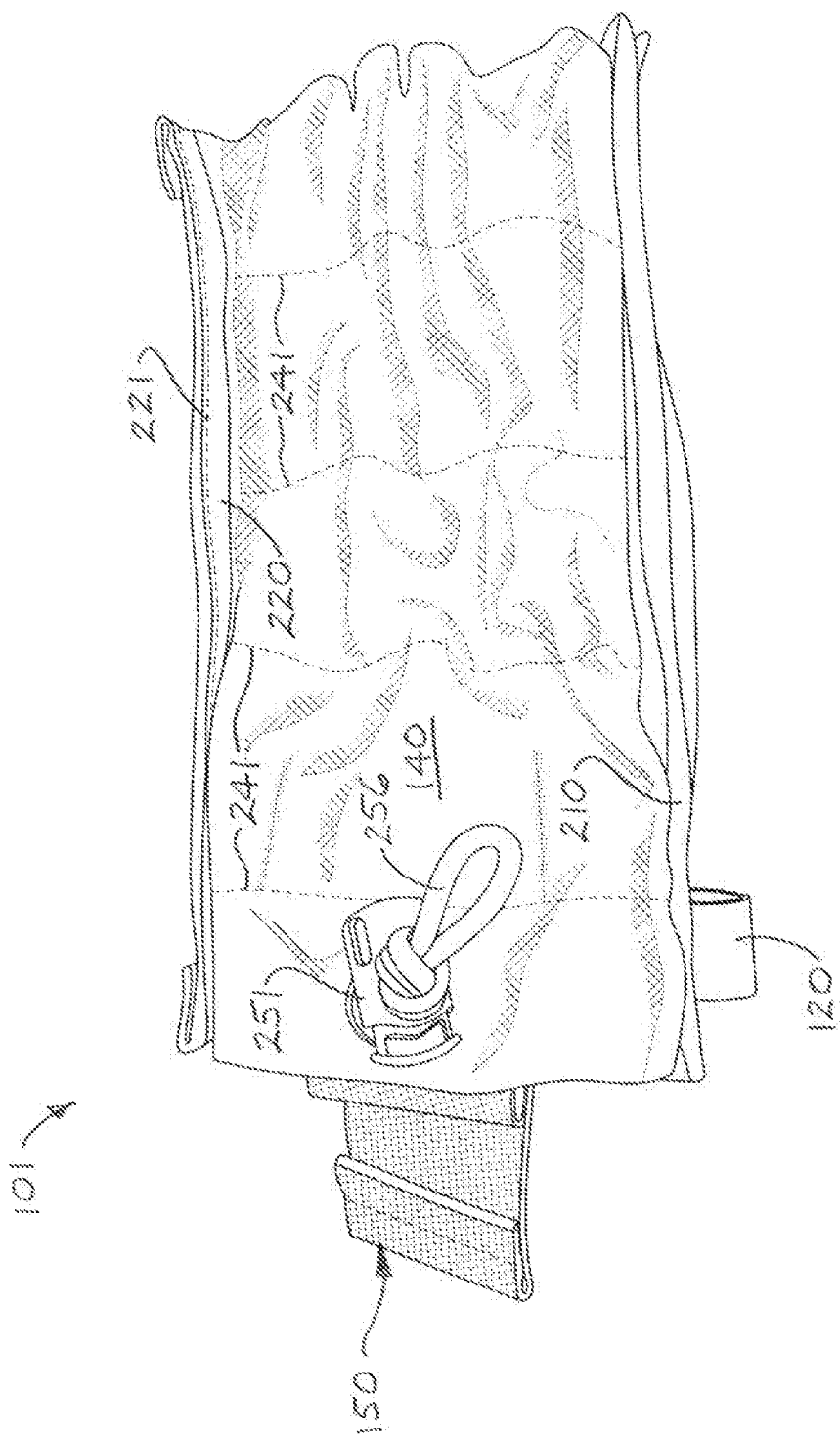
FIG. 19 is a right side view of the illustrative IFAK package assembly illustrated in FIG. 16.
Figure 22:
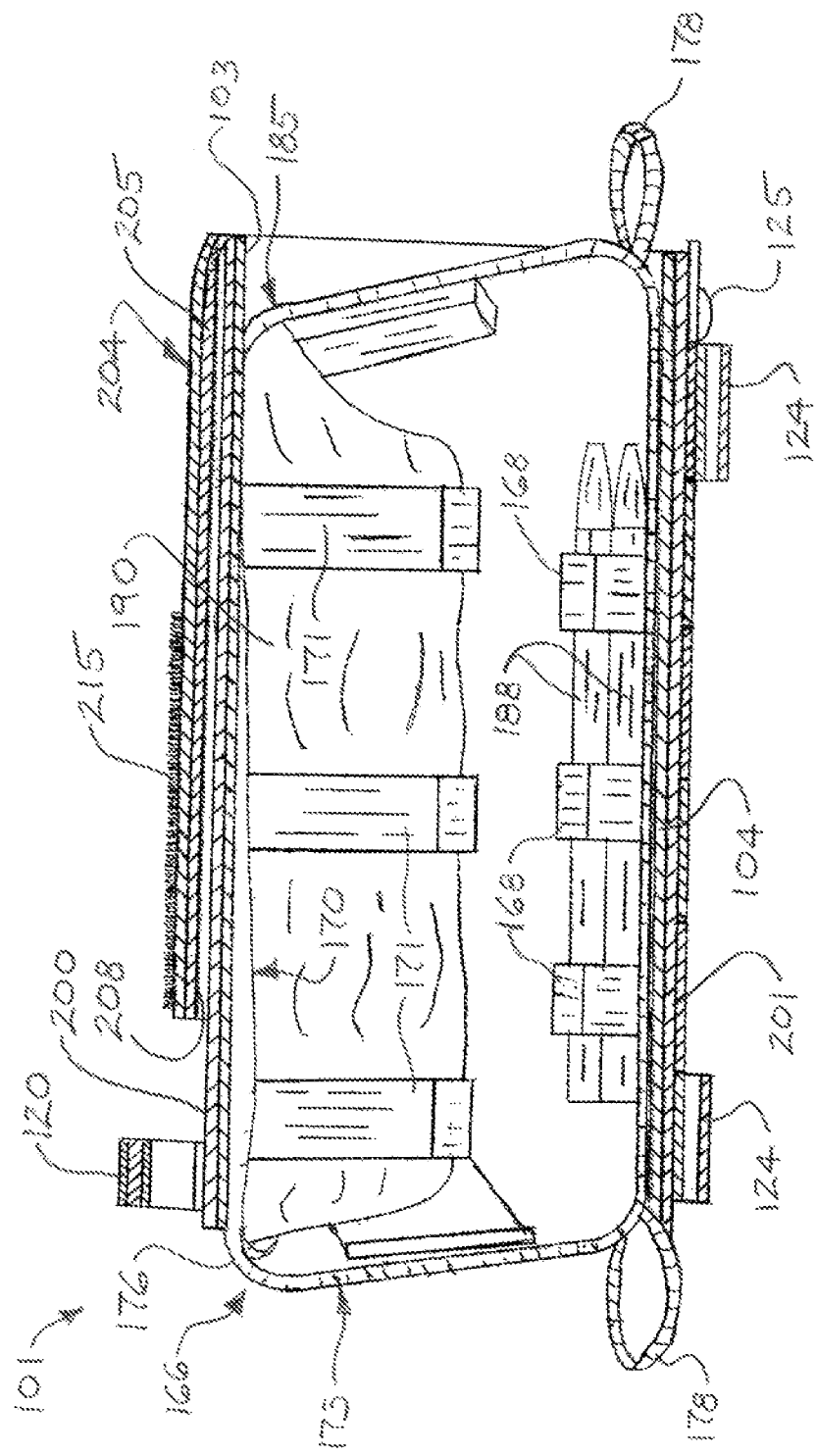
FIG. 22 is a longitudinal sectional view of the outer shell of the IFAK package assembly illustrated in FIG. 16, with the interior sleeve deployed in place in the outer shell.
Figure 23:
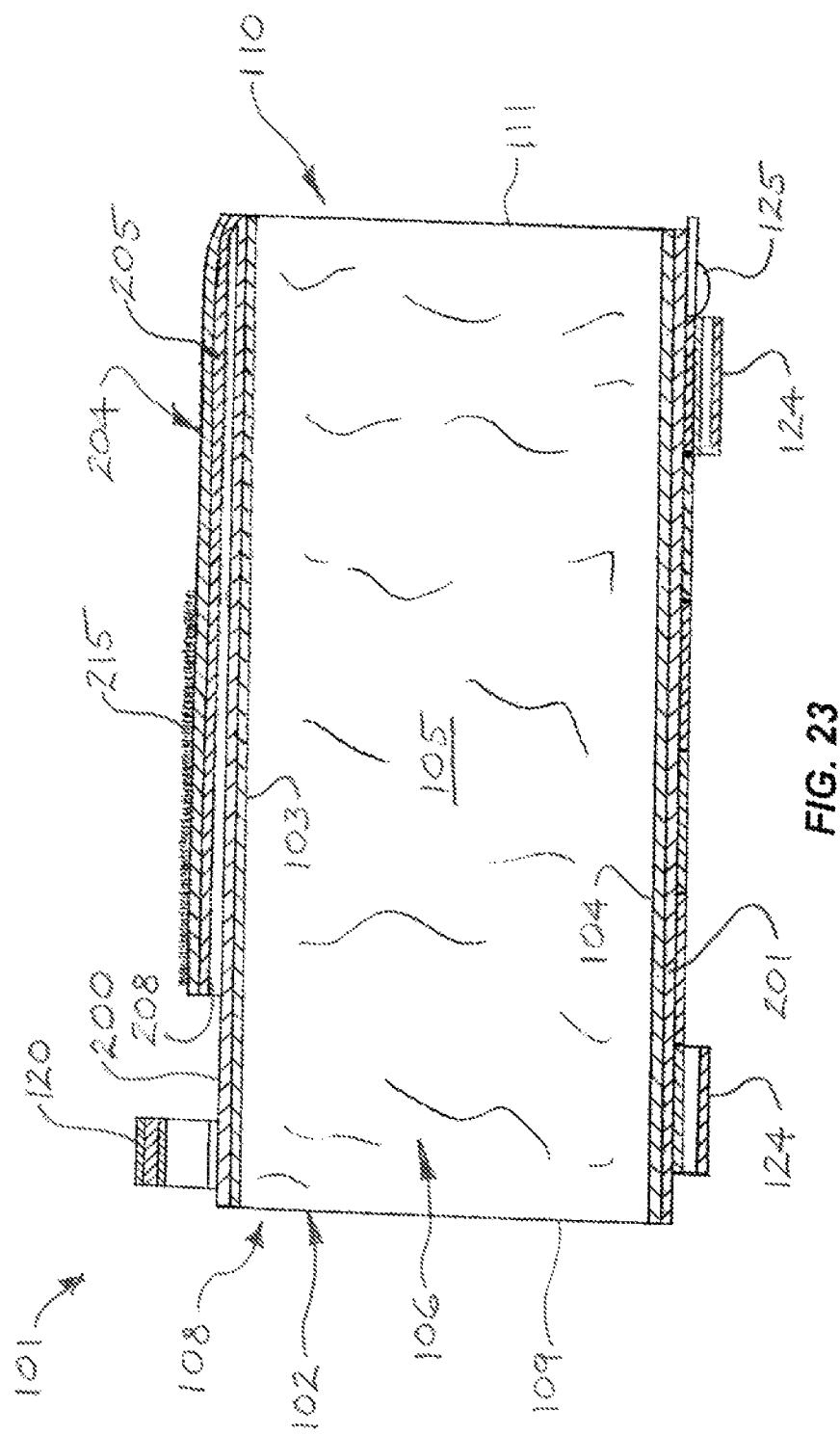
FIG. 23 is a longitudinal sectional, view of the outer shell of the IFAK package assembly illustrated in FIG. 16, with the interior sleeve removed from the outer shell.
Figure 27:
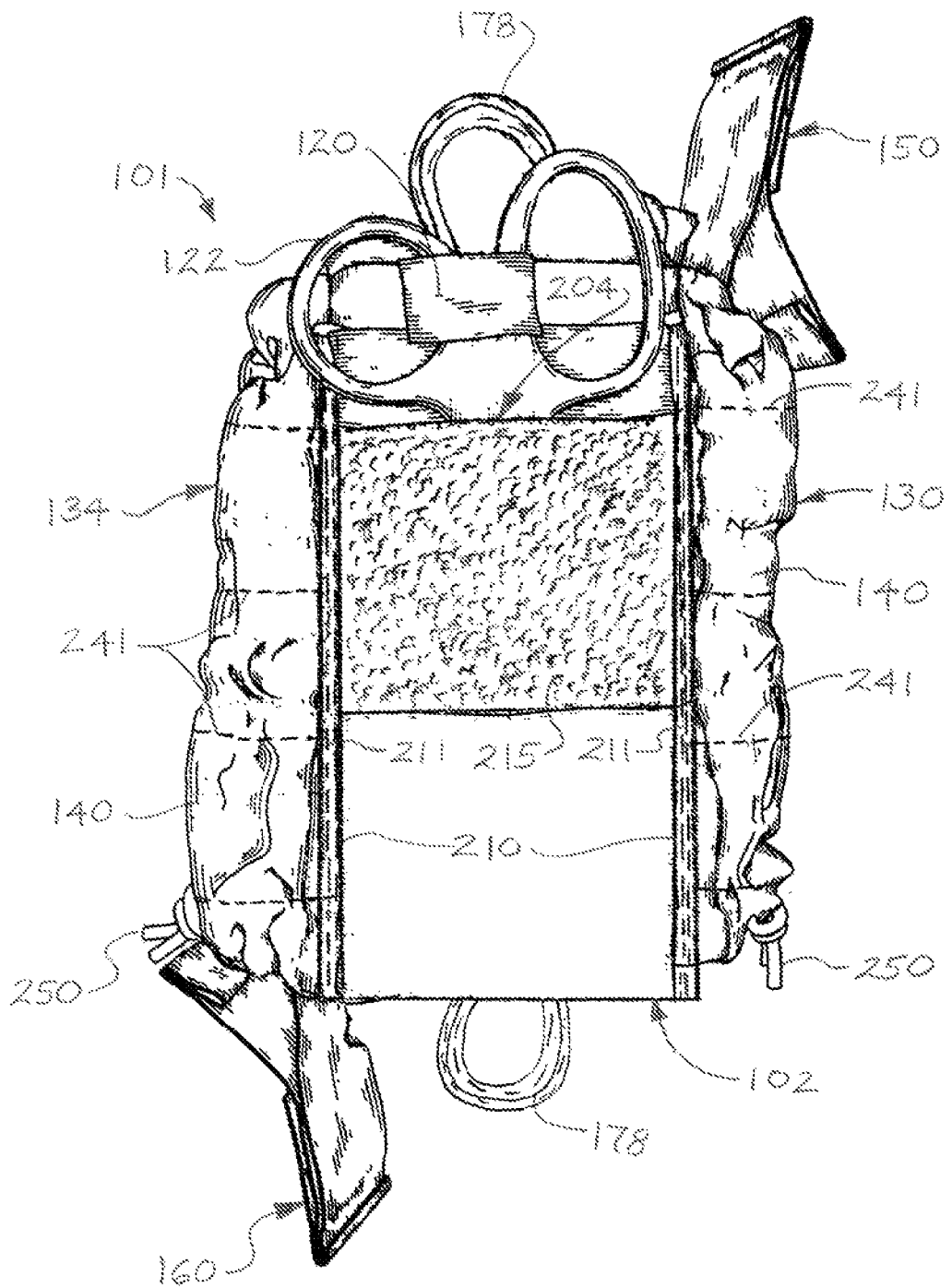
FIG. 27 is a top view of the package assembly illustrated in FIG. 16, with a pair of trauma shears inserted in an exterior shear pocket on the outer shell.

As illustrated in FIG. 16, at least one shear pocket 204 may be provided on the front outer shell wall 103 of the outer shell 102. As illustrated in FIG. 27, the shear pocket 204 may be sized and configured to accommodate at least one pair of trauma shears 122. As illustrated in FIGS. 22 and 23, in some embodiments, the shear pocket 204 may include at least one front exterior shell layer 200 which may be sewn and/or otherwise attached to the front outer shell wall 103 of the outer shell 102. The front exterior shell layer 200 may be doubled over to tartar at least one pocket layer 205 which may be sewn to thrill at least one pocket interior 208 which is sized and configured to accommodate the trauma shears 122. In some embodiments, the side edges of the front exterior shell layer 200 and the side edges of the pocket layer 205 may be sewn or stitched to the front outer shell wall 103 of the outer shell wall 102 via the pair of front seams 210 having the front seam stitching 211 (FIG. 16). At least one securable shear securing strap 120 may be sewn and/or otherwise attached to the front exterior shell layer 200 to secure the trauma shears 122 in the shear pocket 204. In some embodiments, at least one hook and loop fastener surface 215 may be provided on the exterior surface of the shear pocket 204 for the purpose of attaching various accessories knot illustrated) to the shear pocket 204.

Application of the IFAK package assembly 101 may be as was heretofore described with respect to the IFAK package assembly 1 in FIGS. 1-15. The MOLLE straps 123 (FIG. 17) may facilitate mounting of the assembly 101 on MOLLE, whereas the belt loop strap 124 may facilitate mounting of the assembly 101 on a belt (not illustrated) which may be worn by the user. In some embodiments, a rubber-like material (not illustrated) may be provided on the interior surface of the belt loop strap 124 to maintain the IFAK package assembly 101 on the belt worn by the user as the left tourniquet strap 150 or the right tourniquet strap 160 is pulled to retrieve the tourniquet 162 from the corresponding left tourniquet sleeve 130 or right tourniquet sleeve 134. The terminal sleeve compression band 256, center sleeve compression band 258 and sleeve compression cord 250 may normally compress the inner sleeve layer 240 and outer sleeve wall 140 of each left tourniquet sleeve 130 and right tourniquet sleeve 134 toward the corresponding side outer shell wall 105 of the outer shell 102 to secure each tourniquet 162 in the corresponding left sleeve interior 133 and right sleeve interior 137. Each tourniquet 162 may be removed from the corresponding left tourniquet sleeve 130 and right tourniquet sleeve 134 by pulling and detaching the left tourniquet strap 150 and right tourniquet strap 160 from the corresponding interior attachment device 153 as the left tourniquet strap 150 and the right tourniquet strap 160 push the tourniquet 162 from the corresponding left sleeve interior 133 and right sleeve interior 137, typically as was heretofore described. The interior sleeve 166 may be removed from the outer shell interior 106 of the outer shell 102 to access the first aid items 188, 190, typically as was heretofore described with respect to the IFAK package assembly I in FIGS. 1-15.

As illustrated in FIG. 27, in some applications, the trauma shears 178 may be placed in the shear pocket 204 and secured via the shear securing strap 120. The trauma shears 178 may be selectively removed from the shear pocket 204 for use by unfastening the securing strap 120. Various accessory items knot illustrated) may be attached to the hook and loop fastener surface 215 and detached therefrom for use.

While certain illustrative embodiments of the disclosure have been described above, it will be recognized and understood that various modifications can be made to the embodiments and the appended claims are intended to cover all such modifications which may fall within the spirit and scope of the disclosure.

What is claimed is:

1. An individual first aid kit package assembly, comprising:
    an outer shell having a first outer shell end, a second outer shell end, an outer shell interior extending between the first outer shell end and the second outer shell end, a first shell opening at the first outer shell end and a second shell opening at the second outer shell end;
    an interior sleeve removably deployed in the outer shell interior of the outer shell, the interior sleeve selectively removable from a selected one of the first shell opening and the second shell opening;
    a plurality of first aid items carried by the interior sleeve;
    a left tourniquet sleeve carried by a first side of the outer shell, the left tourniquet sleeve having a left sleeve interior configured to contain at least one left tourniquet and a left tourniquet retrieval opening corresponding in position to the first outer shell end of the outer shell;
    a right tourniquet sleeve carried by a second side of the outer shell opposite the first side, the right tourniquet sleeve having a right sleeve interior configured to contain at least one right tourniquet and a right tourniquet retrieval opening corresponding in position to the second outer shell end of the outer shell; and
    the left tourniquet sleeve and the right tourniquet sleeve apply and maintain inward elastic compression into the left sleeve interior and the right sleeve interior, respectively.

2. The assembly of claim 1 wherein the left tourniquet sleeve comprises a left inner sleeve layer, a left outer sleeve wall adjacent to the left inner sleeve layer, a plurality of left sleeve loops between the left inner sleeve layer and the left outer sleeve wall and at least one left sleeve compression band in at least one of the plurality of left sleeve loops and the right tourniquet sleeve comprises a right inner sleeve layer, a right outer sleeve wall adjacent to the right inner sleeve layer, a plurality of right sleeve loops between the right inner sleeve layer and the right outer sleeve wall and at least one right sleeve compression band in at least one of the plurality of right sleeve loops.

3. The assembly of claim 1 further comprising a right tourniquet deployed in place in the right sleeve interior of the right tourniquet sleeve, the right tourniquet selectively retrievable from the right tourniquet sleeve through the right tourniquet retrieval opening; a right tourniquet strap disposed in the right sleeve interior of the right tourniquet sleeve, the right tourniquet strap selectively deployable in a retracted and secured position to surround and secure the right tourniquet in the right tourniquet sleeve and an unsecured position to expose and protrude the right tourniquet from the right tourniquet retrieval opening; and a left tourniquet deployed in place in the left sleeve interior of the left tourniquet sleeve, the left tourniquet selectively retrievable from the left tourniquet sleeve through the left tourniquet retrieval opening; a left tourniquet strap disposed in the left sleeve interior of the left tourniquet sleeve, the left tourniquet strap selectively deployable in a retracted and secured position to surround and secure the left tourniquet in the left tourniquet sleeve and an unsecured position to expose and protrude the left tourniquet from the left tourniquet retrieval opening.

4. The assembly of claim 3 wherein each of the right tourniquet strap and the left tourniquet strap comprises a strap attachment end attached to the outer shell, a main strap segment extending from the strap attachment end and a strap free end terminating the main strap segment, the main strap segment extending from the strap attachment end away from each corresponding one of the right tourniquet retrieval opening and the left tourniquet retrieval opening and across each corresponding one of the right sleeve interior and left sleeve interior toward each corresponding one of right tourniquet retrieval opening and left tourniquet retrieval opening.

5. The assembly of claim 4 further comprising a strap tab extending from the strap free end of the main strap segment, the strap tab protruding from each corresponding one of the right tourniquet retrieval opening and the left tourniquet retrieval opening in the retracted and secured position of each corresponding one of the right tourniquet strap and left tourniquet strap.

6. The assembly of claim 5 further comprising an interior attachment device in each corresponding one of the left sleeve interior and right sleeve interior, a strap terminal segment extending from the strap free end and a strap attachment device carried by the strap terminal segment, the strap attachment device detachably engages the interior attachment device in the retracted and secured position of each corresponding one of the right tourniquet strap and left tourniquet strap.

7. The assembly of claim 6 further comprising a strap pocket in each corresponding one of the left sleeve interior and right sleeve interior, and wherein the interior attachment device is disposed in the strap pocket, and further comprising a strap guide sleeve in each corresponding one of the left sleeve interior and right sleeve interior, and wherein the main strap segment extends through the strap guide sleeve.

8. The assembly of claim 1 further comprising at least one shear pocket on the outer shell.

9. An individual first aid kit package assembly, comprising:
    an outer shell having a first outer shell end, a second outer shell end, an outer shell interior extending between the first outer shell end and the second outer shell end, a first shell opening at the first outer shell end, a second shell opening at the second outer shell end, a front outer shell wall, a rear outer shell wall and a pair of side outer shell walls extending between the front outer shell wall and the rear outer shell wall;
    an interior sleeve removably deployed in the outer shell interior of the outer shell, the interior sleeve selectively removable from a selected one of the first shell opening and the second shell opening;
    a plurality of first aid items carried by the interior sleeve;
    left tourniquet sleeve carried by a first side of the outer shell, the left tourniquet sleeve having a left outer sleeve wall extending from a first corresponding one of the pair of side outer shell walls of the outer shell, a left sleeve interior and a left tourniquet retrieval opening corresponding in position to the first outer shell end of the outer shell;

a left inner sleeve layer adjacent to the left outer sleeve wall;

a first left terminal sleeve loop, a second left terminal sleeve loop and a left center sleeve loop between the left outer sleeve wall and the left inner sleeve layer;

a left terminal sleeve compression band in the first left terminal sleeve loop;

a left center sleeve compression band in the left center sleeve loop;

a left tourniquet deployed in place in the left sleeve interior of the left tourniquet sleeve, the left tourniquet selectively retrievable from the left tourniquet sleeve through the left tourniquet retrieval opening;

a right tourniquet sleeve carried by a second side of the outer shell, the right tourniquet sleeve having a right outer sleeve wall extending from a second corresponding one of the pair of side outer shell walls of the outer shell, the right tourniquet sleeve having a right sleeve interior and a right tourniquet retrieval opening corresponding in position to the second outer shell end of the outer shell;

a right inner sleeve layer adjacent to the right outer sleeve wall;

a first right terminal sleeve loop, a second right terminal sleeve loop and a right center sleeve loop between the right outer sleeve wall and the right inner sleeve layer;

a right terminal sleeve compression band in the first right terminal sleeve loop;

a right center sleeve compression hand in the right center sleeve loop;

a right tourniquet deployed in place in the right sleeve interior of the right tourniquet sleeve, the right tourniquet selectively retrievable from the right tourniquet sleeve through the right tourniquet retrieval opening;

the first left terminal sleeve compression band, the left center sleeve compression band and the second left terminal sleeve compression band apply an inward compression force against the left tourniquet sleeve; and the first right terminal sleeve compression band, the right center sleeve compression hand and the second right terminal sleeve compression band apply an inward compression force against the right tourniquet sleeve.

10. The assembly of claim 9 further comprising a right tourniquet strap disposed in the right sleeve interior of the right tourniquet sleeve, the right tourniquet strap selectively deployable in a retracted and secured position to surround and secure the right tourniquet in the right tourniquet sleeve and an unsecured position to expose and protrude the right tourniquet from the right tourniquet retrieval opening; and a left tourniquet strap disposed in the left sleeve interior of the left tourniquet sleeve, the left tourniquet strap selectively deployable in a retracted and secured position to surround and secure the left tourniquet in the left tourniquet sleeve and an unsecured position to expose and protrude the left tourniquet from the left tourniquet retrieval opening.

11. The assembly of claim 10 wherein each of the right tourniquet strap and the left tourniquet strap comprises a strap attachment end attached to the outer shell, a main strap segment extending from the strap attachment end, and a strap free end terminating the main strap segment, the main strap segment extending from the strap attachment end away from each corresponding one of the right tourniquet retrieval opening and the left tourniquet retrieval opening and across each corresponding one of the right sleeve interior and left sleeve interior toward each corresponding one of right tourniquet retrieval opening and left tourniquet retrieval opening.

12. The assembly of claim 11 further comprising a strap tab extending from the strap free end of the main strap segment, the strap tab protruding from each corresponding one of the right tourniquet retrieval opening and the left tourniquet retrieval opening in the retracted and secured position of each corresponding one of the right tourniquet strap and left tourniquet strap.

13. The assembly of claim 12 further comprising an interior attachment device in each corresponding one of the left sleeve interior and right sleeve interior, a strap terminal segment extending from the strap free end and a strap attachment device carried by the strap terminal segment, the strap attachment device detachably engages the interior attachment device in the retracted and secured position of each corresponding one of die right tourniquet strap and left tourniquet strap.

14. The assembly of claim 13 further comprising a strap pocket in each corresponding one of the left sleeve interior and right sleeve interior, and wherein the interior attachment device is disposed in the strap pocket and further comprising a strap guide sleeve in each corresponding one of the left sleeve interior and right sleeve interior, and wherein the main strap segment extends through the strap guide sleeve.

15. The assembly, of claim 9 further comprising a pair of front seams and a pair of rear seams attaching the left inner sleeve layer, the left outer sleeve wall, the right inner sleeve layer and the right outer sleeve wall to the front outer shell wall and the rear outer shell wall, respectively, of the outer shell.

16. The assembly of claim 9 further comprising at least one shear pocket on the outer shell.

17. An individual first aid kit package assembly, comprising:

an outer shell having a first outer shell end, a second outer shell end, an outer shell interior extending between the first outer shell end and the second outer shell end, a first shell opening at the first outer shell end, a second shell opening at the second outer shell end, a front outer shell wall, a rear outer shell wall and a pair of side outer shell walls extending between the front outer shell wall and the rear outer shell wall;

an interior sleeve removably deployed in the outer shell interior of die outer shell, the interior sleeve selectively removable from a selected one of the first shell opening and the second shell opening, the interior sleeve selectively deployable in an extended configuration facilitating access to the first aid items and a folded configuration facilitating compact placement of the interior sleeve in the outer shell interior of the outer shell, the interior sleeve including a plurality of sleeve sections;

a plurality of first aid items carried by the plurality of sleeve sections of the interior sleeve;

a left tourniquet sleeve carried by a first side of the Outer shell, the left tourniquet sleeve having a left outer sleeve wall extending from a first corresponding one of the pair of side outer shell walls of the outer shell, a left sleeve interior and a left tourniquet retrieval opening corresponding in position to the first outer shell end of the outer shell;

a left inner sleeve layer adjacent to the left outer sleeve wall;

a first left terminal sleeve loop, a second left terminal sleeve loop and a left center sleeve loop between the left outer sleeve wall and the left inner sleeve layer;

a left terminal sleeve compression band in the first left terminal sleeve loop;

a left center sleeve compression band in the left center sleeve loop;

a left tourniquet deployed in place in the left sleeve interior of the left tourniquet sleeve, the left tourniquet selectively retrievable from the left tourniquet sleeve through the left tourniquet retrieval opening;

a right tourniquet sleeve carried by a second side of the outer shell, the right tourniquet sleeve having a right outer sleeve wall extending from a second corresponding one of the pair of side outer shell walls of the outer shell, the right tourniquet sleeve having a right sleeve interior and a right tourniquet retrieval opening corresponding in position to the second outer shell end of the outer shell;

a right inner sleeve layer adjacent to the right outer sleeve wall;

a first right terminal sleeve loop, a second right terminal sleeve loop and a right center sleeve loop between the right outer sleeve wall and the right inner sleeve layer;

a right terminal sleeve compression hand in the first right terminal sleeve loop;

a right center sleeve compression band the right center sleeve loop;

a right tourniquet deployed in place in the right sleeve interior of the right tourniquet sleeve, the right tourniquet selectively retrievable from the right tourniquet sleeve through the right tourniquet retrieval opening;

a pair of front seams and a pair of rear seams attaching the left inner sleeve layer, the left outer sleeve wall, the right inner sleeve layer and the right outer sleeve wall to the front outer shell wall and the rear outer shell wall, respectively, of the outer shell;

the first left terminal sleeve compression band, the left center sleeve compression band and the second left terminal sleeve compression band apply an inward compression force against the left tourniquet sleeve; and the first right terminal sleeve compression band, the right center sleeve compression hand and the second right terminal sleeve compression band apply an inward compression force against the right tourniquet sleeve;

a right tourniquet strap disposed in the right sleeve interior of the right tourniquet sleeve, the right tourniquet strap selectively deployable in a retracted and secured position to surround and secure the right tourniquet in the right tourniquet sleeve and an unsecured position to expose and protrude the right tourniquet from the right tourniquet retrieval opening; and a left tourniquet strap disposed in the left sleeve interior of the left tourniquet sleeve, the left tourniquet strap selectively deployable in a retracted and secured position to surround and secure the left tourniquet in the left tourniquet sleeve and an unsecured position to expose and protrude the left tourniquet from the left tourniquet retrieval opening.

18. The assembly of claim 17 wherein each of the right tourniquet strap and the left tourniquet strap comprises a strap attachment end attached to the outer shell, a main strap segment extending from the strap attachment end and a strap free end terminating the main strap segment, the main strap segment extending from the strap attachment end away from each corresponding one of the right tourniquet retrieval opening and the left tourniquet retrieval opening and across each corresponding one of the right sleeve interior and left sleeve interior toward each corresponding one of right tourniquet retrieval opening and left tourniquet retrieval opening.

19. The assembly of claim 18 further comprising a strap tab extending from the strap free end of the main strap segment, the strap tab protruding from each corresponding one of the right tourniquet retrieval opening and the left tourniquet retrieval opening in the retracted and secured position of each corresponding one of the right tourniquet strap and left tourniquet strap.

20. The assembly of claim 19 further comprising an interior attachment device in each corresponding one of the left sleeve interior and right sleeve interior, a strap terminal segment extending from the strap free end and a strap attachment device carried by the strap terminal segment, the strap attachment device detachably engages the interior attachment device in the retracted and secured position of each corresponding one of the right tourniquet strap and left tourniquet strap; a strap pocket in each corresponding one of the let t sleeve interior and right sleeve interior, and wherein the interior attachment device is disposed in the strap pocket; and a strap guide sleeve in each corresponding one of the left sleeve interior and right sleeve interior, and wherein the main strap segment extends through the strap guide sleeve.

* * * * *